(12) United States Patent
Kwok et al.

(10) Patent No.: US 10,752,672 B1
(45) Date of Patent: Aug. 25, 2020

(54) RECOMBINANT HEMOGLOBINS AND METHODS OF PREPARATION AND USE THEREOF

(71) Applicant: Cheer Global Limited, Hong Kong (CN)

(72) Inventors: Sui Yi Kwok, Hong Kong (CN); Norman Fung Man Wai, Vancouver (CA); Shan Yu, Hong Kong (CN); Terence Shau Yin Wai, Vancouver (CA)

(73) Assignee: Cheer Global Limited, Hong Kong (CN)

( * ) Notice: Subject to any disclaimer, the term of this patent is extended or adjusted under 35 U.S.C. 154(b) by 0 days.

(21) Appl. No.: 16/777,932

(22) Filed: Jan. 31, 2020

Related U.S. Application Data

(60) Provisional application No. 62/799,829, filed on Feb. 1, 2019.

(51) Int. Cl.
| | |
|---|---|
| *A61K 38/17* | (2006.01) |
| *C07K 14/435* | (2006.01) |
| *C07K 14/805* | (2006.01) |
| *C12N 1/20* | (2006.01) |
| *C12P 21/00* | (2006.01) |

(52) U.S. Cl.
CPC .............. *C07K 14/805* (2013.01); *C12N 1/20* (2013.01); *C12P 21/00* (2013.01)

(58) Field of Classification Search
CPC ... A61K 38/17; A61K 38/1709; C07K 14/435
See application file for complete search history.

(56) References Cited

U.S. PATENT DOCUMENTS 9,814,759 B2    11/2017   Wong et al.

OTHER PUBLICATIONS

A human recombinant haemoglobin designed for use as a blood substitute.
International Search Report and Written Opinion of PCT application No. PCT/CN2020/074173 issued from the International Search Authority dated Apr. 24, 2020.
Looker et al.; A human recombinant haemoglobin designed for use as a blood substitute; Nature; vol. 356; Mar. 19, 1992; pp. 258-260.
Looker et al.; Accession No. 1O1J_A; Genpept; Aug. 28, 2017.
Looker et al.; Accession No. 1O1J_B; Genpept; Aug. 28, 2017.
Soman et al.; Accession No. 5SW7_B; GenPept ; Oct. 19, 2017.

*Primary Examiner* — Maryam Monshipouri
(74) *Attorney, Agent, or Firm* — Spruson & Ferguson (Hong Kong) Limited

(57) ABSTRACT

The present disclosure relates to recombinant hemoglobins with improved oxygen carrying capacity and methods of preparation and use thereof. The present disclosure also relates to a pharmaceutical composition including the recombinant hemoglobin useful for treating oxygen deficiency related diseases or conditions, such as stroke, hemorrhagic shock, peripheral arterial disease (PAD), acute mountain sickness (AMS), cancer, and Parkinson's disease (PD).

21 Claims, 21 Drawing Sheets
Specification includes a Sequence Listing.

di-alpha chain (SEQ ID NO: 1)

MLSPADKTNVKAAWGKVGAHAGEYGAEAFERMFLSFPTTKTYFPHFDLSHGSAQVKGQGK

KVADALTNAVAHVDDMPNALSALSDLHAHKLRVDPVNFKLLSHCLLVTLAAHLPAEFTPA

VHASLDKFLASVSTVLTSKYRGMLSPADKTNVKAAWGKVGAHAGEYGAEAFERMFLSFPT

TKTYFPHFDLSHGSAQVKGQGKKVADALTNAVAHVDDMPNALSALSDLHAHKLRVDPVNF

KLLSHCLLVTLAAHLPAEFTPAVHASLDKFLASVSTVLTSKYR beta chain used in TBM1 (SEQ ID NO: 2)

MHLTPEEKSAVTALWGKVNVDEVGGEALGRLLVVYPWTQRFFESFGDLSTPDAVMGNPKV

KAHGKKVLGAFSDGLAHLDNLKGTFATLSELHCDKLHVDPENFRLLGNVLVCVLAHHFGK

EFTPPVQAAYQKVVAGVANALAHKYH beta chain used in TBM9 (SEQ ID NO: 3)

MHLTPEEKSAVTALWGKVNVDEVGGEALGRLLVVYPWTQRFFESFGDLSTPDAVMGNPKV

KAHGKKVLGAFSDGLAHLDNLDGTFATLSELHCDKLHVDPENFRLLGKVLVCVLAHHFGK

EFTPPVQAAYQKVVAGVANALAHKYH di-alpha chain used in TBN (SEQ ID NO: 11)

MLSPADKTNVKAAWGKVGAHAGEYGAEALERMFLSFPTTKTYFPHFDLSHGSAQVKGHGK

KVADALTNAVAHVDDMPNALSALSDLHAHKLRVDPVNFKLLSHCLLVTLAAHLPAEFTPA

VHASLDKFLASVSTVLTSKYRGMLSPADKTNVKAAWGKVGAHAGEYGAEALERMFLSFPT

TKTYFPHFDLSHGSAQVKGHGKKVADALTNAVAHVDDMPNALSALSDLHAHKLRVDPVNF

KLLSHCLLVTLAAHLPAEFTPAVHASLDKFLASVSTVLTSKYR beta chain used in TBN (SEQ ID NO: 12)

MHLTPEEKSAVTALWGKVNVDEVGGEALGRLLVVYPWTQRFFESFGDLSTPDAVMGNPKV

KAHGKKVLGAFSDGLAHLDNLKGTFATLSELHCDKLHVDPENFRLLGNVLVCVLAHHFGK

EFTPPVQAAYQKVVAGVANALAHKYH

FIG. 1

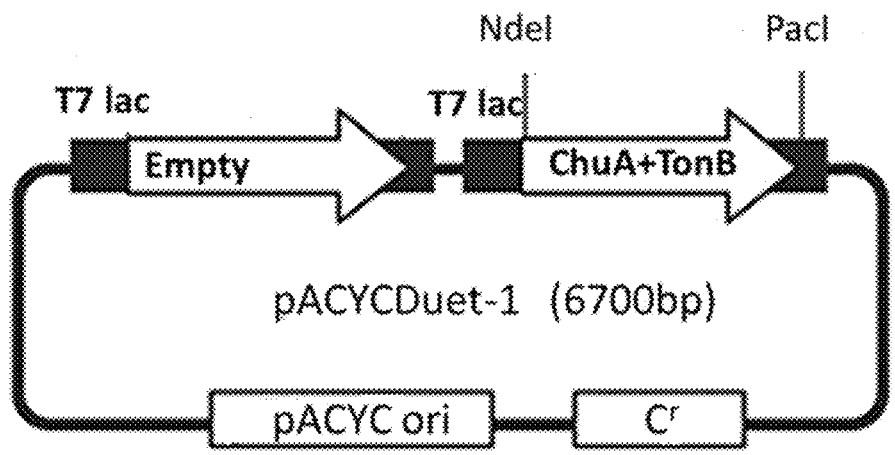
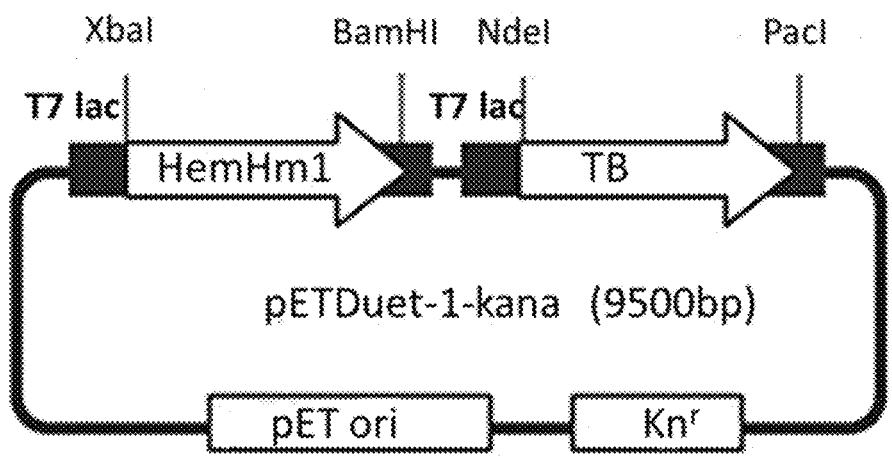
FIG. 2A

| Sample | 2,3-DPG (mM) | p50 Raw | p50 Adair | Hill Mean | Hill Max |
|---|---|---|---|---|---|
| TBN | 0 | 9.03 | 9.05 | 1.58 | 2.04 |
| TBM1 | 0 | 17.15 | 17.27 | 1.53 | 2.00 |
| TBM9 | 0 | 32.07 | 36.25 | 1.42 | 1.94 |
| TBN | 4 | 15.07 | 14.19 | 1.63 | 1.97 |
| TBM1 | 4 | 24.52 | 25.77 | 1.62 | 2.01 |
| TBM9 | 4 | 38.85 | 44.23 | 1.52 | 1.95 |

FIG. 5B

SEQ ID NO: 8 (HemH mutant)

ATGTCGCGTAAGAAGATGGGATTGCTGGTGATGGCTTACGGGACGCCTTACAAAGAAGAGGACATTGAG
CGTTACTATACGCACATCCGTCGTGGGCGTAAGCCTGAGCCTGAGATGCTTCAGGATCTGAAAGATCGCTA
CGAGGCTATCGGGGGTATTTCTCCTTTGGCACAGATTACCAAACAACAAGCCCATAATCTTGAACAACATCT
GAATGAAATTCAAGACGAAATTACCTTCAAGGCCTACATTGGCTTGAAACATATTGAGCCTTTTATCGAGG
ATGCCGTGGCTGAAATGCATAAGGATGGAATCACCGAAGCCGTTTCTATCGTGCTGGCCCCACATTTTTCC
ACGTTCTCAGTACAAAGCTACAATAAACGCGCAAAAGAAGAAGCCGAGAAGCTTGGGGGCTTGACAATCA
CCTCTGTCGAATCATGGTATGATGAACCGAAATTCGTTACCTATTGGGTTGACCGTGTAAAGGAGACCTAT
GCCAGTATGCCCGAGGATGAACGCGAAAACGCCATGTTAATCGTTAGTGCTCACTCGCAACCGGAGAAAA
TCAAAGAATTTGGTGACCCGTACCCTGACCAGCTTCACGAGTCGGCAAAACTGATTGCCGAAGGAGCGGA
TGTTTCGGAATACGCTGTTGGTTGGCAAAGTGAGGGAAATACGCCAGACCCTTGGCTGGGTCCGGATGTC
CAAGACTTAACCCGTGATCTGTTCGAGCAGAAAGGTTATCAGGCGTTCGTATATGTGCCCGTGGGCTTCGT
GGCTGATCATCTGGAGGTCTTGTATGATAATGACTATGAGTGCAAGGTGGTCACAGACGATATCGGGGCA
TCGTATTATCGCCCGGAGATGCCAAATGCTAAACCGGAATTTATTGACGCCTTGGCTACGGTTGTACTTAAA
AAACTTGGCCGCTAA

SEQ ID NO: 13 (HemH mutant)

MSRKKMGLLVMAYGTPYKEEDIERYYTHIRRGRKPEPEMLQDLKDRYEAIGGISPLAQITKQQAHNLEQHLNEI
QDEITFKAYIGLKHIEPFIEDAVAEMHKDGITEAVSIVLAPHFSTFSVQSYNKRAKEEAEKLGGLTITSVESWYDEP
KFVTYWVDRVKETYASMPEDERENAMLIVSAHSQPEKIKEFGDPYPDQLHESAKLIAEGADVSEYAVGWQSEG
NTPDPWLGPDVQDLTRDLFEQKGYQAFVYVPVGFVADHLEVLYDNDYECKVVTDDIGASYYRPEMPNAKPEFI
DALATVVLKKLGR

FIG. 7

SEQ ID NO: 9 (ChuA)

ATGTCACGTCCGCAATTTACCTCGTTGCGTTTGAGTTTATTGGCCTTAGCTGTTTCTGCCACCTTGCCAACGTT
TGCTTTTGCTACTGAAACCATGACCGTTACGGCAACGGGGAATGCCCGTAGTTCCTTCGAAGCGCCTATGATG
GTCAGCGTCATCGACACTTCCGCTCCTGAAAATCAAACGGCTACTTCAGCCACCGATCTGCTGCGTCATGTTC
CTGGAATTACTCTGGATGGTACCGGACGAACCAACGGTCAGGATGTAAATATGCGTGGCTATGATCATCGCGG
CGTGCTGGTTCTTGTCGATGGTGTTCGTCAGGGAACGGATACCGGACACCTGAATGGCACTTTTCTCGATCC
GGCGCTGATCAAGCGTGTTGAGATTGTTCGTGGACCTTCAGCATTACTGTATGGCAGTGGCGCGCTGGGTGG
AGTGATCTCCTACGATACGGTCGATGCAAAAGATTTATTGCAGGAAGGACAAAGCAGTGGTTTTCGTGTCTTT
GGTACTGGCGGCACGGGGGACCATAGCCTGGGATTAGGCGCGAGCGCGTTTGGGCGAACTGAAAATCTGG
ATGGTATTGTGGCCTGGTCCAGTCGCGATCGGGGTGATTTACGCCAGAGCAATGGTGAAACCGCGCCGAATG
ACGAGTCCATTAATAACATGCTGGCGAAAGGGACCTGGCAAATTGATTCAGCCCAGTCTCTGAGCGGTTTAG
TGCGTTACTACAACAACGACGCGCGTGAACCAAAAAATCCGCAGACCGTTGGGGCTTCTGAAAGCAGCAAC
CCGATGGTTGATCGTTCAACAATTCAACGCGATGCGCAGCTTTCTTATAAACTCGCCCCGCAGGGCAACGACT
GGTTAAATGCAGATGCAAAAATTTATTGGTCGGAAGTCCGTATTAATGCGCAAAACACGGGGAGTTCCGGCG
AGTATCGTGAACAGATAACAAAAGGAGCCAGGCTGGAGAACCGTTCCACTCTCTTTGCCGACAGTTTCGCTT
CTCACTTACTGACGTATGGCGGTGAGTATTATCGTCAGGAACAACATCCGGGCGGCGCGACGACGGGCTTCC
CGCAAGCAAAAATCGATTTTAGCTCCGGCTGGCTACAGGATGAGATCACCTTACGCGATCTGCCGATTACCCT
GCTTGGCGGAACCCGCTATGACAGTTATCGCGGTAGCAGTGACGGTTACAAAGATGTTGATGCCGACAAATG
GTCATCTCGTGCGGGGATGACTATCAATCCGACTAACTGGCTGATGTTATTTGGCTCTTATGCCCAGGCATTCC
GCGCCCCGACGATGGGCGAAATGTATAACGATTCTAAGCACTTCTCGATTGGTCGCTTCTATACCAACTATTGG
GTGCCAAACCCGAACTTACGTCCGGAAACTAACGAAACTCAGGAGTACGGTTTTGGGCTGCGTTTTGATGAC
CTGATGTTGTCCAATGATGCTCTGGAATTTAAAGCCAGCTACTTTGATACCAAAGCGAAGGATTACATCTCCAC
GACCGTCGATTTCGCGGCGGCGACGACTATGTCGTATAACGTCCCGAACGCCAAAATCTGGGGCTGGGATGT
GATGACGAAATATACCACTGATCTGTTTAGCCTTGATGTGGCCTATAACCGTACCCGCGGCAAAGACACCGAT
ACCGGCGAATACATCTCCAGCATTAACCCGGATACTGTTACCAGCACTCTGAATATTCCGATCGCTCACAGTGG
CTTCTCTGTTGGGTGGGTTGGTACGTTTGCCGATCGCTCAACACATATCAGCAGCAGTTACAGCAAACAACCA
GGCTATGGCGTGAATGATTTCTACGTCAGTTATCAAGGACAACAGGCGCTCAAAGGTATGACCACTACTTTGG
TGTTGGGTAACGCTTTCGACAAAGAGTACTGGTCGCCGCAAGGCATCCCACAGGATGGTCGTAACGGAAAA
ATTTTCGTGAGTTATCAATGGTAA

SEQ ID NO: 14 (ChuA)

MSRPQFTSLRLSLLALAVSATLPTFAFATETMTVTATGNARSSFEAPMMVSVIDTSAPENQTATSATDLLRHVP
GITLDGTGRTNGQDVNMRGYDHRGVLVLVDGVRQGTDTGHLNGTFLDPALIKRVEIVRGPSALLYGSGALGG
VISYDTVDAKDLLQEGQSSGFRVFGTGGTGDHSLGLGASAFGRTENLDGIVAWSSRDRGDLRQSNGETAPNDE
SINNMLAKGTWQIDSAQSLSGLVRYYNNDAREPKNPQTVGASESSNPMVDRSTIQRDAQLSYKLAPQGNDW
LNADAKIYWSEVRINAQNTGSSGEYREQITKGARLENRSTLFADSFASHLLTYGGEYYRQEHPGGATTGFPQA
KIDFSSGWLQDEITLRDLPITLLGGTRYDSYRGSSDGYKDVDADKWSSRAGMTINPTNWLMLFGSYAQAFRAP
TMGEMYNDSKHFSIGRFYTNYWVPNPNLRPETNETQEYGFGLRFDDLMLSNDALEFKASYFDTKAKDYISTTV
DFAAATTMSYNVPNAKIWGWDVMTKYTTDLFSLDVAYNRTRGKDTDTGEYISSINPDTVTSTLNIPIAHSGFSV
GWVGTFADRSTHISSSYSKQPGYGVNDFYVSYQGQQALKGMTTTLVLGNAFDKEYWSPQGIPQDGRNGKIFV
SYQW

FIG. 8

SEQ ID NO: 10 (TonB)

ATGACCCTTGATTTACCTCGCCGCTTCCCCTGGCCGACGTTACTTTCGGTCTGCATTCATGGTGCTGTTGTGGC
GGGTCTGCTCTATACCTCGGTACATCAGGTTATTGAACTACCTGCGCCTGCGCAGCCGATTTCTGTCACGATGG
TTGCGCCTGCTGATCTCGAACCGCCACAAGCCGTTCAGCCGCCACCGGAGCCGGTGGTAGAGCCAGAACCG
GAACCTGAGCCGATCCCCGAACCGCCAAAAGAAGCACCGGTGGTCATTGAAAAGCCGAAGCCGAAACCTAA
GCCAAAACCGAAGCCGGTGAAAAAGGTACAGGAGCAGCAAAAACGCGATGTCAAACCCGTAGAGTCGCGT
CCGGCATCACCGTTTGAAAATACGGCACCGGCACGCCCGACATCAAGTACAGCAACGGCTGCAACCAGCAA
GCCGGTTACCAGTGTGGCTTCAGGACCACGCGCATTAAGCCGTAATCAGCCGCAGTATCCGGCACGAGCACA
GGCATTGCGCATTGAAGGGCAGGTTAAAGTTAAATTTGACGTCACGCCGGATGGTCGCGTGGATAACGTACA
AATCCTCTCAGCCAAGCCTGCGAACATGTTTGAGCGTGAGGTGAAAAATGCGATGCGCAGATGGCGTTATGA
GCCGGGTAAGCCAGGCAGTGGGATTGTGGTGAATATCCTGTTTAAAATTAACGGCACCACCGAAATTCAGTA
A

SEQ ID NO: 15 (TonB)

MTLDLPRRFPWPTLLSVCIHGAVVAGLLYTSVHQVIELPAPAQPISVTMVAPADLEPPQAVQPPPEPVVEPEPE
PEPIPEPPKEAPVVIEKPKPKPKPKPVKKVQEQQKRDVKPVESRPASPFENTAPARPTSSTATAATSKPVTSVA
SGPRALSRNQPQYPARAQALRIEGQVKVKFDVTPDGRVDNVQILSAKPANMFEREVKNAMRRWRYEPGKPG
SGIVVNILFKINGTTEIQ

FIG. 9

| Recombinant Hemoglobin | Protein conc. by Bradford (mg/ml) | $K_{az}(h^{-1})$ |
|---|---|---|
| TBN | 1.05 | 0.1327 |
| TBM1 | 1.00 | 0.0757 |
| TBM9 | 1.08 | 0.0743 |

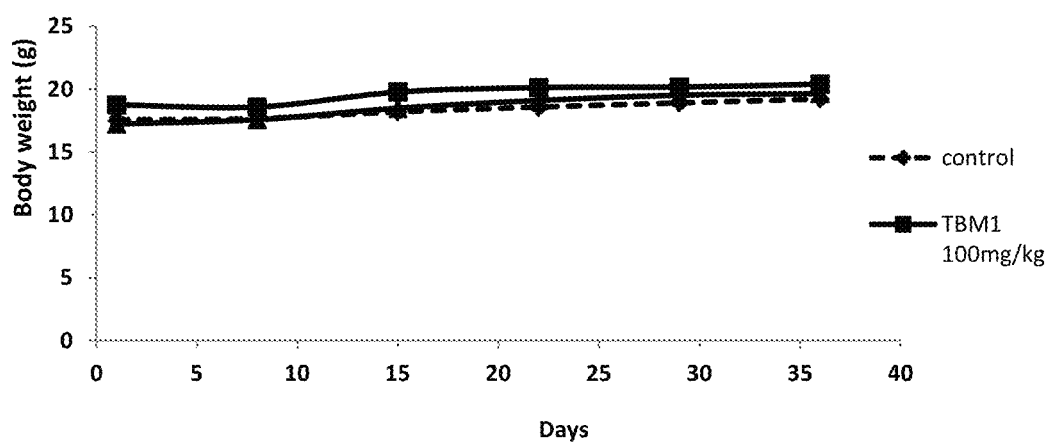
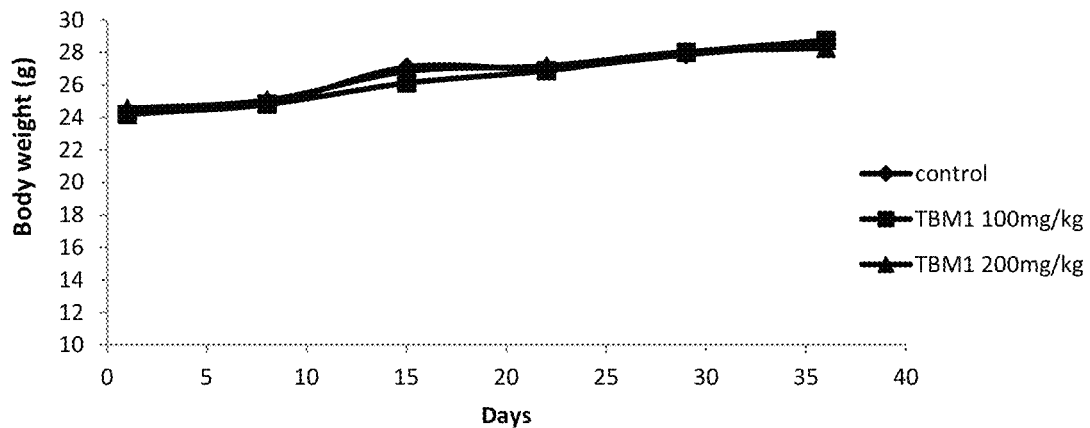
FIG. 14

SEQUENCE LISTING

```
<160> NUMBER OF SEQ ID NOS: 15

<210> SEQ ID NO 1
<211> LENGTH: 283
<212> TYPE: PRT
<213> ORGANISM: Artificial Sequence
<220> FEATURE:
<223> OTHER INFORMATION: di-alpha chain, synthesized in lab

<400> SEQUENCE: 1

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Phe Glu Arg Met
                20                  25                  30

Phe Leu Ser Phe Pro Thr Thr Lys Thr Tyr Phe Pro His Phe Asp Leu
            35                  40                  45

Ser His Gly Ser Ala Gln Val Lys Gly Gln Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg Gly Met Leu
    130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Phe Glu Arg Met Phe Leu
                165                 170                 175

Ser Phe Pro Thr Thr Lys Thr Tyr Phe Pro His Phe Asp Leu Ser His
            180                 185                 190

Gly Ser Ala Gln Val Lys Gly Gln Gly Lys Lys Val Ala Asp Ala Leu
        195                 200                 205

Thr Asn Ala Val Ala His Val Asp Asp Met Pro Asn Ala Leu Ser Ala
    210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

Ala Glu Phe Thr Pro Ala Val His Ala Ser Leu Asp Lys Phe Leu Ala
            260                 265                 270

Ser Val Ser Thr Val Leu Thr Ser Lys Tyr Arg
        275                 280
```

```
<210> SEQ ID NO 2
<211> LENGTH: 146
<212> TYPE: PRT
<213> ORGANISM: Artificial Sequence
<220> FEATURE:
<223> OTHER INFORMATION: beta chain, synthesized in lab

<400> SEQUENCE: 2

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 146
<212> TYPE: PRT
<213> ORGANISM: Artificial Sequence
<220> FEATURE:
<223> OTHER INFORMATION: beta chain, synthesized in lab

<400> SEQUENCE: 3

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Asp Gly Thr Phe Ala Thr Leu Ser Glu Leu His Cys Asp Lys Leu
                85                  90                  95

His Val Asp Pro Glu Asn Phe Arg Leu Leu Gly Lys Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
```

<210> SEQ ID NO 4
<211> LENGTH: 852
<212> TYPE: DNA
<213> ORGANISM: Artificial Sequence
<220> FEATURE:
<223> OTHER INFORMATION: di-alpha chain, synthesized in lab

<400> SEQUENCE: 4

| | |
|---|---|
| atgctgtctc cggcagataa aacgaatgtt aaagcagcct ggggtaaagt cggcgctcac | 60 |
| gcgggcgaat acggtgcaga agcctttgaa cgtatgtttc tgtccttccc gaccacgaaa | 120 |
| acctattttc cgcatttcga tctgagtcac ggctccgcgc aggtgaaagg tcagggcaaa | 180 |
| aaagttgcag acgctctgac gaacgcggtg gcccacgttg atgacatgcc gaatgcactg | 240 |
| tcagctctga gcgatctgca cgcgcacaaa ctgcgtgttg atccggtgaa ctttaaactg | 300 |
| ctgagccatt gcctgctggt caccctggcg gcacacctgc cggcagaatt tacgccggcg | 360 |
| gttcatgcca gctggataa attcctgcg agcgtgagca ccgtcctgac gtctaaatac | 420 |
| cgcggcatgc tgtctccggc agataaaacg aatgttaaag cagcctgggg taaagtcggc | 480 |
| gctcacgcgg gcgaatacgg tgcagaagcc tttgaacgta tgtttctgtc cttcccgacc | 540 |
| acgaaaacct attttccgca tttcgatctg agtcacggct ccgcgcaggt gaaaggtcag | 600 |
| ggcaaaaaag ttgcagacgc tctgacgaac gcggtggccc acgttgatga catgccgaat | 660 |
| gcactgtcag ctctgagcga tctgcacgcg cacaaactgc gtgttgatcc ggtgaacttt | 720 |
| aaactgctga gccattgcct gctggtcacc ctggcggcac acctgccggc agaatttacg | 780 |
| ccggcggttc atgccagcct ggataaattc ctggcgagcg tgagcaccgt cctgacgtct | 840 |
| aaataccgct aa | 852 |

<210> SEQ ID NO 5
<211> LENGTH: 441
<212> TYPE: DNA
<213> ORGANISM: Artificial Sequence
<220> FEATURE:
<223> OTHER INFORMATION: beta chain, synthesized in lab

<400> SEQUENCE: 5

| | |
|---|---|
| atgcatctga ccccggaaga aaaatcggct gtgacggctc tgtggggcaa agttaatgtg | 60 |
| gacgaagtcg gcggcgaagc actgggccgt ctgctggttg tgtatccgtg gacccagcgc | 120 |
| tttttcgaat cttttggtga tctgtctacg ccggacgctg ttatgggcaa cccgaaagtc | 180 |
| aaagcgcatg gcaaaaaagt cctgggtgcc tttagtgatg gcctggcaca cctggacaat | 240 |
| ctgaaaggca ccttcgcgac gctgagcgaa ctgcattgcg ataaactgca cgtggacccg | 300 |
| gaaaacttcc gtctgctggg taatgttctg gtctgtgtgc tggcccatca ctttggcaaa | 360 |
| gaatttaccc cgccggtgca ggcggcctat caaaaagtcg tggcaggcgt tgcaaacgct | 420 |
| ctggcgcata ataccacta a | 441 |

<210> SEQ ID NO 6
<211> LENGTH: 441
<212> TYPE: DNA
<213> ORGANISM: Artificial Sequence
<220> FEATURE:
<223> OTHER INFORMATION: beta chain, synthesized in lab

<400> SEQUENCE: 6

| | |
|---|---|
| atgcatctga ccccggaaga aaaatcggct gtgacggctc tgtggggcaa agttaatgtg | 60 |

```
gacgaagtcg gcggcgaagc actgggccgt ctgctggttg tgtatccgtg gacccagcgc    120
ttttccgaat cttttggtga tctgtctacg ccggacgctg ttatgggcaa cccgaaagtc    180
aaagcgcatg gcaaaaaagt cctgggtgcc tttagtgatg gcctggcaca cctggacaat    240
ctggacggca ccttcgcgac gctgagcgaa ctgcattgcg ataaactgca cgtggacccg    300
gaaaacttcc gtctgctggg taaagttctg gtctgtgtgc tggcccatca ctttggcaaa    360
gaatttaccc cgccggtgca ggcggcctat caaaaagtcg tggcaggcgt tgcaaacgct    420
ctggcgcata ataccacta a                                                441

<210> SEQ ID NO 7
<211> LENGTH: 933
<212> TYPE: DNA
<213> ORGANISM: Artificial Sequence
<220> FEATURE:
<223> OTHER INFORMATION: HemH wildtype, synthesized in lab

<400> SEQUENCE: 7
atgtcgcgta agaagatggg attgctggtg atggcttacg ggacgcctta caagaagag    60 gacattgagc gttactatac gcacatccgt cgtgggcgta agcctgagcc tgagatgctt    120
caggatctga agatcgcta cgaggctatc gggggtattt ctcctttggc acagattacc    180
gaacaacaag cccataatct tgaacaacat ctgaatgaaa ttcaagacga aattaccttc    240
aaggcctaca ttggcttgaa acatattgag cctttatcg aggatgccgt ggctgaaatg    300
cataaggatg gaatcaccga agccgtttct atcgtgctgg ccccacattt ttccacgttc    360
tcagtacaaa gctacaataa acgcgcaaaa gaagaagccg agaagcttgg gggcttgaca    420
atcacctctg tcgaatcatg gtatgatgaa ccgaaattcg ttacctattg ggttgaccgt    480
gtaaaggaga ccctatgccag tatgcccgag gatgaacgcg aaaacgccat gttaatcgtt    540
agtgctcact cgctaccgga gaaaatcaaa gaatttggtg acccgtaccc tgaccagctt    600
cacgagtcgg caaaactgat tgccgaagga gcgggtgttt cggaatacgc tgttggttgg    660
caaagtgagg gaaatacgcc agacccttgg ctgggtccgg atgtccaaga cttaacccgt    720
gatctgttcg agcagaaagg ttatcaggcg ttcgtatatg tgcccgtggg cttcgtggct    780
gatcatctgg aggtcttgta tgataatgac tatgagtgca aggtggtcac agacgatatc    840
ggggcatcgt tatcgcccc ggagatgcca atgctaaac cggaatttat tgacgccttg    900
gctacggttg tacttaaaaa acttggccgc taa                                  933

<210> SEQ ID NO 8
<211> LENGTH: 933
<212> TYPE: DNA
<213> ORGANISM: Artificial Sequence
<220> FEATURE:
<223> OTHER INFORMATION: HemH mutant, synthesized in lab

<400> SEQUENCE: 8
atgtcgcgta agaagatggg attgctggtg atggcttacg ggacgcctta caagaagag    60 gacattgagc gttactatac gcacatccgt cgtgggcgta agcctgagcc tgagatgctt    120
caggatctga agatcgcta cgaggctatc gggggtattt ctcctttggc acagattacc    180
aaacaacaag cccataatct tgaacaacat ctgaatgaaa ttcaagacga aattaccttc    240
aaggcctaca ttggcttgaa acatattgag cctttatcg aggatgccgt ggctgaaatg    300
cataaggatg gaatcaccga agccgtttct atcgtgctgg ccccacattt ttccacgttc    360
```

| | |
|---|---|
| tcagtacaaa gctacaataa acgcgcaaaa gaagaagccg agaagcttgg gggcttgaca | 420 |
| atcacctctg tcgaatcatg gtatgatgaa ccgaaattcg ttacctattg ggttgaccgt | 480 |
| gtaaaggaga cctatgccag tatgcccgag gatgaacgcg aaaacgccat gttaatcgtt | 540 |
| agtgctcact cgcaaccgga gaaaatcaaa gaattcggtg acccgtaccc tgaccagctt | 600 |
| cacgagtcgg caaaactgat tgccgaagga gcggatgttt cggaatacgc tgttggttgg | 660 |
| caaagtgagg gaaatacgcc agacccttgg ctgggtccgg atgtccaaga cttaacccgt | 720 |
| gatctgttcg agcagaaagg ttatcaggcg ttcgtatatg tgcccgtggg cttcgtggct | 780 |
| gatcatctgg aggtcttgta tgataatgac tatgagtgca aggtggtcac agacgatatc | 840 |
| ggggcatcgt attatcgccc ggagatgcca aatgctaaac cggaattcat tgacgccttg | 900 |
| gctacggttg tacttaaaaa acttggccgc taa | 933 |

<210> SEQ ID NO 9
<211> LENGTH: 1983
<212> TYPE: DNA
<213> ORGANISM: Artificial Sequence
<220> FEATURE:
<223> OTHER INFORMATION: ChuA, Synthesized in lab

<400> SEQUENCE: 9

| | |
|---|---|
| atgtcacgtc cgcaatttac ctcgttgcgt ttgagtttat tggccttagc tgtttctgcc | 60 |
| accttgccaa cgtttgcttt tgctactgaa ccatgaccg ttacggcaac ggggaatgcc | 120 |
| cgtagttcct tcgaagcgcc tatgatggtc agcgtcatcg acacttccgc tcctgaaaat | 180 |
| caaacggcta cttcagccac cgatctgctg cgtcatgttc ctggaattac tctggatggt | 240 |
| accggacgaa ccaacggtca ggatgtaaat atgcgtggct atgatcatcg cggcgtgctg | 300 |
| gttcttgtcg atggtgttcg tcagggaacg gataccggac acctgaatgg cacttttctc | 360 |
| gatccggcgc tgatcaagcg tgttgagatt gttcgtggac cttcagcatt actgtatggc | 420 |
| agtggcgcgc tgggtggagt gatctcctac gatacggtcg atgcaaaaga tttattgcag | 480 |
| gaaggacaaa gcagtggttt tcgtgtctt ggtactggcg gcacggggga ccatagcctg | 540 |
| ggattaggcg cgagcgcgtt tgggcgaact gaaaatctgg atggtattgt ggcctggtcc | 600 |
| agtcgcgatc ggggtgattt acgccagagc aatggtgaaa ccgcgccgaa tgacgagtcc | 660 |
| attaataaca tgctggcgaa agggacctgg caaattgatt cagcccagtc tctgagcggt | 720 |
| ttagtgcgtt actacaacaa cgacgcgcgt gaaccaaaaa atccgcagac cgttggggct | 780 |
| tctgaaagca gcaaccccgat ggttgatcgt tcaacaattc aacgcgatgc gcagctttct | 840 |
| tataaactcg ccccgcaggg caacgactgg ttaaatgcag atgcaaaaat ttattggtcg | 900 |
| gaagtccgta ttaatgcgca aaacacgggg agttccggcg agtatcgtga acagataaca | 960 |
| aaaggagcca ggctggagaa ccgttccact ctctttgccg acagtttcgc ttctcactta | 1020 |
| ctgacgtatg gcggtgagta ttatcgtcag gaacaacatc cgggcggcgc gacgacgggc | 1080 |
| ttcccgcaag caaaaatcga ttttagctcc ggctggctac aggatgagat caccttacgc | 1140 |
| gatctgccga ttaccctgct tggcggaacc cgctatgaca gttatcgcgg tagcagtgac | 1200 |
| ggttacaaag atgttgatgc cgacaaatgg tcatctcgtg cggggatgac tatcaatccg | 1260 |
| actaactggc tgatgttatt tggctcttat gcccaggcat tccgcgcccc gacgatgggc | 1320 |
| gaaatgtata cgattctaa gcacttctcg attggtcgct tctataccaa ctattgggtg | 1380 |
| ccaaacccga acttacgtcc ggaaactaac gaaactcagg agtacggttt tgggctgcgt | 1440 |
| tttgatgacc tgatgttgtc caatgatgct ctggaattta agccagcta ctttgatacc | 1500 |

-continued

```
aaagcgaagg attacatctc cacgaccgtc gatttcgcgg cggcgacgac tatgtcgtat    1560
aacgtcccga acgccaaaat ctggggctgg gatgtgatga cgaaatatac cactgatctg    1620
tttagccttg atgtggccta taaccgtacc cgcggcaaag acaccgatac cggcgaatac    1680
atctccagca ttaaccccgga tactgttacc agcactctga atattccgat cgctcacagt    1740
ggcttctctg ttgggtgggt tggtacgttt gccgatcgct caacacatat cagcagcagt    1800
tacagcaaac aaccaggcta tggcgtgaat gatttctacg tcagttatca aggacaacag    1860
gcgctcaaag gtatgaccac tactttggtg ttgggtaacg ctttcgacaa agagtactgg    1920
tcgccgcaag gcatcccaca ggatggtcgt aacggaaaaa ttttcgtgag ttatcaatgg    1980
taa                                                                    1983
```

<210> SEQ ID NO 10
<211> LENGTH: 720
<212> TYPE: DNA
<213> ORGANISM: Artificial Sequence
<220> FEATURE:
<223> OTHER INFORMATION: TonB, Synthesized in lab

<400> SEQUENCE: 10

```
atgacccttg atttacctcg ccgcttcccc tggccgacgt tactttcggt ctgcattcat      60
ggtgctgttg tggcgggtct gctctatacc tcggtacatc aggttattga actacctgcg     120
cctgcgcagc cgatttctgt cacgatggtt gcgcctgctg atctcgaacc gccacaagcc     180
gttcagccgc caccggagcc ggtggtagag ccagaaccgg aacctgagcc gatccccgaa     240
ccgccaaaag aagcaccggt ggtcattgaa aagccgaagc cgaaacctaa gccaaaaccg     300
aagccggtga aaaaggtaca ggagcagcaa aaacgcgatg tcaaaccgt agagtcgcgt      360 ccggcatcac cgtttgaaaa tacggcaccg gcacgcccga catcaagtac agcaacggct     420
gcaaccagca agccggttac cagtgtggct tcaggaccac gcgcattaag ccgtaatcag     480
ccgcagtatc cggcacgagc acaggcattg cgcattgaag ggcaggttaa agttaaattt     540
gacgtcacgc cggatggtcg cgtggataac gtacaaatcc tctcagccaa gcctgcgaac     600
atgtttgagc gtgaggtgaa aaatgcgatg cgcagatggc gttatgagcc gggtaagcca     660
ggcagtggga ttgtggtgaa tatcctgttt aaaattaacg gcaccaccga aattcagtaa     720
```

<210> SEQ ID NO 11
<211> LENGTH: 283
<212> TYPE: PRT
<213> ORGANISM: Artificial Sequence
<220> FEATURE:
<223> OTHER INFORMATION: Di-alpha chain, Synthesized in lab

<400> SEQUENCE: 11

```
Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
```

```
                        85                  90                  95
Asn Phe Lys Leu Leu Ser His Cys Leu Leu Val Thr Leu Ala Ala His
                100                 105                 110

Leu Pro Ala Glu Phe Thr Pro Ala Val His Ala Ser Leu Asp Lys Phe
            115                 120                 125

Leu Ala Ser Val Ser Thr Val Leu Thr Ser Lys Tyr Arg Gly Met Leu
        130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Leu Glu Arg Met Phe Leu
                165                 170                 175

Ser Phe Pro Thr Thr Lys Thr Tyr Phe Pro His Phe Asp Leu Ser His
                180                 185                 190

Gly Ser Ala Gln Val Lys Gly His Gly Lys Lys Val Ala Asp Ala Leu
            195                 200                 205

Thr Asn Ala Val Ala His Val Asp Asp Met Pro Asn Ala Leu Ser Ala
        210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

Ala Glu Phe Thr Pro Ala Val His Ala Ser Leu Asp Lys Phe Leu Ala
                260                 265                 270

Ser Val Ser Thr Val Leu Thr Ser Lys Tyr Arg
            275                 280

<210> SEQ ID NO 12
<211> LENGTH: 146
<212> TYPE: PRT
<213> ORGANISM: Artificial Sequence
<220> FEATURE:
<223> OTHER INFORMATION: beta chain, Synthesized in lab

<400> SEQUENCE: 12

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
                20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
                100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
        130                 135                 140

Tyr His
145
```

-continued

```
<210> SEQ ID NO 13
<211> LENGTH: 310
<212> TYPE: PRT
<213> ORGANISM: Artificial Sequence
<220> FEATURE:
<223> OTHER INFORMATION: HemH mutant, synthesized in the lab

<400> SEQUENCE: 13

Met Ser Arg Lys Lys Met Gly Leu Leu Val Met Ala Tyr Gly Thr Pro
1               5                   10                  15

Tyr Lys Glu Glu Asp Ile Glu Arg Tyr Tyr Thr His Ile Arg Arg Gly
                20                  25                  30

Arg Lys Pro Glu Pro Glu Met Leu Gln Asp Leu Lys Asp Arg Tyr Glu
            35                  40                  45

Ala Ile Gly Gly Ile Ser Pro Leu Ala Gln Ile Thr Lys Gln Gln Ala
        50                  55                  60

His Asn Leu Glu Gln His Leu Asn Glu Ile Gln Asp Glu Ile Thr Phe
65                  70                  75                  80

Lys Ala Tyr Ile Gly Leu Lys His Ile Glu Pro Phe Ile Glu Asp Ala
                85                  90                  95

Val Ala Glu Met His Lys Asp Gly Ile Thr Glu Ala Val Ser Ile Val
            100                 105                 110

Leu Ala Pro His Phe Ser Thr Phe Ser Val Gln Ser Tyr Asn Lys Arg
        115                 120                 125

Ala Lys Glu Glu Ala Glu Lys Leu Gly Gly Leu Thr Ile Thr Ser Val
    130                 135                 140

Glu Ser Trp Tyr Asp Glu Pro Lys Phe Val Thr Tyr Trp Val Asp Arg
145                 150                 155                 160

Val Lys Glu Thr Tyr Ala Ser Met Pro Glu Asp Glu Arg Glu Asn Ala
                165                 170                 175

Met Leu Ile Val Ser Ala His Ser Gln Pro Glu Lys Ile Lys Glu Phe
            180                 185                 190

Gly Asp Pro Tyr Pro Asp Gln Leu His Glu Ser Ala Lys Leu Ile Ala
        195                 200                 205

Glu Gly Ala Asp Val Ser Glu Tyr Ala Val Gly Trp Gln Ser Glu Gly
    210                 215                 220

Asn Thr Pro Asp Pro Trp Leu Gly Pro Asp Val Gln Asp Leu Thr Arg
225                 230                 235                 240

Asp Leu Phe Glu Gln Lys Gly Tyr Gln Ala Phe Val Tyr Val Pro Val
                245                 250                 255

Gly Phe Val Ala Asp His Leu Glu Val Leu Tyr Asp Asn Asp Tyr Glu
            260                 265                 270

Cys Lys Val Val Thr Asp Asp Ile Gly Ala Ser Tyr Tyr Arg Pro Glu
        275                 280                 285

Met Pro Asn Ala Lys Pro Glu Phe Ile Asp Ala Leu Ala Thr Val Val
    290                 295                 300

Leu Lys Lys Leu Gly Arg
305                 310

<210> SEQ ID NO 14
<211> LENGTH: 660
<212> TYPE: PRT
<213> ORGANISM: Artificial Sequence
<220> FEATURE:
<223> OTHER INFORMATION: ChuA, Synthesized in lab

<400> SEQUENCE: 14
```

```
Met Ser Arg Pro Gln Phe Thr Ser Leu Arg Leu Ser Leu Leu Ala Leu
1               5                   10                  15

Ala Val Ser Ala Thr Leu Pro Thr Phe Ala Phe Ala Thr Glu Thr Met
            20                  25                  30

Thr Val Thr Ala Thr Gly Asn Ala Arg Ser Ser Phe Glu Ala Pro Met
        35                  40                  45

Met Val Ser Val Ile Asp Thr Ser Ala Pro Glu Asn Gln Thr Ala Thr
    50                  55                  60

Ser Ala Thr Asp Leu Leu Arg His Val Pro Gly Ile Thr Leu Asp Gly
65                  70                  75                  80

Thr Gly Arg Thr Asn Gly Gln Asp Val Asn Met Arg Gly Tyr Asp His
                85                  90                  95

Arg Gly Val Leu Val Leu Val Asp Gly Val Arg Gln Gly Thr Asp Thr
            100                 105                 110

Gly His Leu Asn Gly Thr Phe Leu Asp Pro Ala Leu Ile Lys Arg Val
        115                 120                 125

Glu Ile Val Arg Gly Pro Ser Ala Leu Leu Tyr Gly Ser Gly Ala Leu
    130                 135                 140

Gly Gly Val Ile Ser Tyr Asp Thr Val Asp Ala Lys Asp Leu Leu Gln
145                 150                 155                 160

Glu Gly Gln Ser Ser Gly Phe Arg Val Phe Gly Thr Gly Thr Gly
                165                 170                 175

Asp His Ser Leu Gly Leu Gly Ala Ser Ala Phe Gly Arg Thr Glu Asn
                180                 185                 190

Leu Asp Gly Ile Val Ala Trp Ser Ser Arg Asp Arg Gly Asp Leu Arg
                195                 200                 205

Gln Ser Asn Gly Glu Thr Ala Pro Asn Asp Glu Ser Ile Asn Asn Met
    210                 215                 220

Leu Ala Lys Gly Thr Trp Gln Ile Asp Ser Ala Gln Ser Leu Ser Gly
225                 230                 235                 240

Leu Val Arg Tyr Tyr Asn Asn Asp Ala Arg Glu Pro Lys Asn Pro Gln
                245                 250                 255

Thr Val Gly Ala Ser Glu Ser Ser Asn Pro Met Val Asp Arg Ser Thr
            260                 265                 270

Ile Gln Arg Asp Ala Gln Leu Ser Tyr Lys Leu Ala Pro Gln Gly Asn
    275                 280                 285

Asp Trp Leu Asn Ala Asp Ala Lys Ile Tyr Trp Ser Glu Val Arg Ile
    290                 295                 300

Asn Ala Gln Asn Thr Gly Ser Ser Gly Glu Tyr Arg Glu Gln Ile Thr
305                 310                 315                 320

Lys Gly Ala Arg Leu Glu Asn Arg Ser Thr Leu Phe Ala Asp Ser Phe
            325                 330                 335

Ala Ser His Leu Leu Thr Tyr Gly Gly Glu Tyr Tyr Arg Gln Glu Gln
        340                 345                 350

His Pro Gly Gly Ala Thr Thr Gly Phe Pro Gln Ala Lys Ile Asp Phe
    355                 360                 365

Ser Ser Gly Trp Leu Gln Asp Glu Ile Thr Leu Arg Asp Leu Pro Ile
    370                 375                 380

Thr Leu Leu Gly Gly Thr Arg Tyr Asp Ser Tyr Arg Gly Ser Ser Asp
385                 390                 395                 400

Gly Tyr Lys Asp Val Asp Ala Asp Lys Trp Ser Ser Arg Ala Gly Met
            405                 410                 415

Thr Ile Asn Pro Thr Asn Trp Leu Met Leu Phe Gly Ser Tyr Ala Gln
```

```
            420                 425                 430
Ala Phe Arg Ala Pro Thr Met Gly Glu Met Tyr Asn Asp Ser Lys His
            435                 440                 445

Phe Ser Ile Gly Arg Phe Tyr Thr Asn Tyr Trp Val Pro Asn Pro Asn
            450                 455                 460

Leu Arg Pro Glu Thr Asn Glu Thr Gln Glu Tyr Gly Phe Gly Leu Arg
465                 470                 475                 480

Phe Asp Asp Leu Met Leu Ser Asn Asp Ala Leu Glu Phe Lys Ala Ser
                    485                 490                 495

Tyr Phe Asp Thr Lys Ala Lys Asp Tyr Ile Ser Thr Thr Val Asp Phe
                500                 505                 510

Ala Ala Ala Thr Thr Met Ser Tyr Asn Val Pro Asn Ala Lys Ile Trp
            515                 520                 525

Gly Trp Asp Val Met Thr Lys Tyr Thr Thr Asp Leu Phe Ser Leu Asp
            530                 535                 540

Val Ala Tyr Asn Arg Thr Arg Gly Lys Asp Thr Asp Thr Gly Glu Tyr
545                 550                 555                 560

Ile Ser Ser Ile Asn Pro Asp Thr Val Thr Ser Thr Leu Asn Ile Pro
                    565                 570                 575

Ile Ala His Ser Gly Phe Ser Val Gly Trp Val Gly Thr Phe Ala Asp
                580                 585                 590

Arg Ser Thr His Ile Ser Ser Ser Tyr Ser Lys Gln Pro Gly Tyr Gly
            595                 600                 605

Val Asn Asp Phe Tyr Val Ser Tyr Gln Gly Gln Gln Ala Leu Lys Gly
            610                 615                 620

Met Thr Thr Thr Leu Val Leu Gly Asn Ala Phe Asp Lys Glu Tyr Trp
625                 630                 635                 640

Ser Pro Gln Gly Ile Pro Gln Asp Gly Arg Asn Gly Lys Ile Phe Val
                    645                 650                 655

Ser Tyr Gln Trp
                660

<210> SEQ ID NO 15
<211> LENGTH: 239
<212> TYPE: PRT
<213> ORGANISM: Artificial Sequence
<220> FEATURE:
<223> OTHER INFORMATION: TonB, Synthesized in lab

<400> SEQUENCE: 15

Met Thr Leu Asp Leu Pro Arg Arg Phe Pro Trp Pro Thr Leu Leu Ser
1               5                   10                  15

Val Cys Ile His Gly Ala Val Ala Gly Leu Leu Tyr Thr Ser Val
                    20                  25                  30

His Gln Val Ile Glu Leu Pro Ala Pro Ala Gln Pro Ile Ser Val Thr
            35                  40                  45

Met Val Ala Pro Ala Asp Leu Glu Pro Gln Ala Val Gln Pro
        50                  55                  60

Pro Glu Pro Val Val Glu Pro Glu Pro Glu Pro Ile Pro Glu
65                  70                  75                  80

Pro Pro Lys Glu Ala Pro Val Val Ile Glu Lys Pro Lys Pro Lys Pro
                    85                  90                  95

Lys Pro Lys Pro Lys Pro Val Lys Lys Val Gln Glu Gln Gln Lys Arg
                100                 105                 110

Asp Val Lys Pro Val Glu Ser Arg Pro Ala Ser Pro Phe Glu Asn Thr
```

-continued

```
            115                 120                 125
Ala Pro Ala Arg Pro Thr Ser Ser Thr Ala Thr Ala Ala Thr Ser Lys
        130                 135                 140

Pro Val Thr Ser Val Ala Ser Gly Pro Arg Ala Leu Ser Arg Asn Gln
145                 150                 155                 160

Pro Gln Tyr Pro Ala Arg Ala Gln Ala Leu Arg Ile Glu Gly Gln Val
                165                 170                 175

Lys Val Lys Phe Asp Val Thr Pro Asp Gly Arg Val Asp Asn Val Gln
            180                 185                 190

Ile Leu Ser Ala Lys Pro Ala Asn Met Phe Glu Arg Glu Val Lys Asn
        195                 200                 205

Ala Met Arg Arg Trp Arg Tyr Glu Pro Gly Lys Pro Gly Ser Gly Ile
    210                 215                 220

Val Val Asn Ile Leu Phe Lys Ile Asn Gly Thr Thr Glu Ile Gln
225                 230                 235
```

RECOMBINANT HEMOGLOBINS AND METHODS OF PREPARATION AND USE THEREOF

CROSS-REFERENCE TO RELATED APPLICATIONS

This application claims the benefit of priority of U.S. Provisional Application No. 62/799,829, filed on Feb. 1, 2019, the contents of which are hereby incorporated by reference in their entirety for all purposes.

TECHNICAL FIELD

The present disclosure generally relates to recombinant hemoglobins and methods preparation, purification, and use thereof. The present disclosure further relates to pharmaceutical compositions comprising the recombinant hemoglobins and methods of using the recombinant hemoglobin-based pharmaceutical composition to treat oxygen deficiency related diseases, such stroke, hemorrhagic shock, peripheral arterial disease (PAD) and acute mountain sickness (AMS), and other diseases or conditions, such as cancer and Parkinson's disease (PD).

BACKGROUND

Hemoglobin (Hb) is an oxygen-carrying protein enriched in red blood cells (erythrocytes) that delivers oxygen to body tissues via blood flow through the circulatory system. The oxygen-carrying protein comprises four associated polypeptide chains (two alpha chains and two beta chains), and bears a group known as heme whose iron atom temporarily binds to oxygen in the lungs and releases it throughout the body. Hemoglobin can also bind carbon monoxide (CO) to form (carbonmonoxy)hemoglobin (HbCO), which can reduce the total amount of Hb that is available to deliver oxygen to the body.

Hypoxia is common in cancers and can lead to ionizing radiation and chemotherapy resistance by depriving tumor cells of the oxygen essential for the cytotoxic activities of these agents. Hypoxia may also reduce tumor sensitivity to radiation therapy and chemotherapy through one or more indirect mechanisms that include proteomic and genomic changes.

Hemoglobin extracted from red blood cells has been used as a blood substitute for oxygen delivery to hypoxic tissues. However, the use of unmodified cell-free Hb purified from red blood cells can suffer from several limitations, such as contamination, supply limitations, an increase in oxygen affinity due to loss of the cofactor 2,3-disphosphoglycerate (2,3-DPG), and dissociation of Hb tetramers into aP dimers, which are cleared by renal filtration and can cause long-term kidney damage.

The development of improved recombinant hemoglobins can solve some or all of the above-mentioned problems. However, existing recombinant hemoglobins can suffer from low oxygen carrying capacity, and the existing methods for preparing recombinant hemoglobins are laborious and can suffer from poor soluble yields of hemoglobin with high percentages of impurities. For example, protoporphyrin-IX (PPIX), a common byproduct in conventional recombinant hemoglobin production, can impair the overall oxygen carrier function of the recombinant hemoglobins.

Existing methods for preparing recombinant hemoglobins generally include a heat treatment step to remove impurities, such as PPIX. However, the incorporation of a heat treatment step into the preparation method can increase cost and reduce yield of the protein product. In addition, in order to maintain the stability of the recombinant hemoglobins during the heat treatment and downstream processes thereof, CO is required for the recombinant hemoglobins. However, since CO is undesired in the final product, a CO removal step is usually required for existing preparation methods, which also makes the existing methods costly and time-consuming.

Therefore, there is a need for improved recombinant hemoglobins with high oxygen carrying capacity, and there is also a need for simplified methods for preparing recombinant hemoglobins with high yield and high purity.

SUMMARY

The present disclosure generally relates to recombinant hemoglobins and methods of use and preparation thereof. The recombinant hemoglobins described herein can have improved oxygen-carrying capacity. The disclosed recombinant hemoglobins are useful for treating diseases, such as cancer, stroke, hemorrhagic shock, acute mountain sickness (AMS), peripheral arterial disease (PAD) and Parkinson's disease (PD).

The present disclosure also generally relates to methods of preparing the recombinant hemoglobins described herein. The recombinant hemoglobins prepared using the methods described herein can have reduced amounts of PPIX, little or no HbCO, and an optimal heme/protein ratio and tetramer/dimer distribution.

In a first aspect of the present disclosure, there is provided a recombinant hemoglobin comprising a di-alpha chain and two beta chains, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine.

In a first embodiment of the first aspect of the present disclosure, the di-alpha chain comprises a polypeptide sequence having at least 99.29% sequence homology with SEQ ID NO: 1.

In a second embodiment of the first aspect of the present disclosure, the di-alpha chain comprises a polypeptide having at least 99.64% sequence homology with SEQ ID NO: 1.

In a third embodiment of the first aspect of the present disclosure, the di-alpha chain is a polypeptide sequence having SEQ ID NO: 1.

In a fourth embodiment of the first aspect of the present disclosure, each of the two beta chains comprises a polypeptide sequence having at least 97.94% sequence homology with SEQ ID NO: 2, wherein the amino acid at position 1 must be methionine.

In a fifth embodiment of the first aspect of the present disclosure, each of the two beta chains is a polypeptide sequence having SEQ ID NO: 2.

In a sixth embodiment of the first aspect of the present disclosure, each of the two beta chains comprises a polypeptide sequence having at least 97.94% sequence homology with SEQ ID NO: 3, wherein the amino acid at position 1 must be methionine, the amino acid at position 82 must be aspartic acid, and the amino acid at position 108 must be lysine.

In a seventh embodiment of the first aspect of the present disclosure, each of the two beta chains comprises a polypeptide sequence having at least 98.63% sequence homology with SEQ ID NO: 3.

In an eighth embodiment of the first aspect of the present disclosure, each of the two beta chains comprises a polypeptide sequence having at least 99.31% sequence homology with SEQ ID NO: 3.

In a ninth embodiment of the first aspect of the present disclosure, each of the two beta chains comprises a polypeptide sequence of SEQ ID NO: 3.

In a second aspect of the present disclosure, there is provided a pharmaceutical composition comprising the above-mentioned recombinant hemoglobin and at least one pharmaceutically acceptable carrier.

In a third aspect of the present disclosure, there is provided a method of treating an oxygen deficiency related disease in a subject in need thereof comprising the step of administering a therapeutically effective amount of the pharmaceutical composition to the subject.

In a first embodiment of the third aspect of the present disclosure, the oxygen deficiency related disease comprises cancer, stroke, hemorrhagic shock, acute mountain sickness (AMS), peripheral arterial disease (PAD) or Parkinson's disease (PD).

In a fourth aspect of the present disclosure, there is provided a method of producing the recombinant hemoglobin, comprising the steps of:
(a) providing a host cell comprising a polynucleotide encoding the di-alpha chain and a polynucleotide encoding the beta chain; and
(b) inducing the host cell containing the polynucleotide encoding the di-alpha chain and the polynucleotide encoding the beta chain to express recombinant hemoglobin thereby producing the recombinant hemoglobin.

In a first embodiment of the fourth aspect of the present disclosure, the polynucleotide encoding the di-alpha chain and the polynucleotide encoding the beta chain comprise a polynucleotide sequence of SEQ ID NO: 4 and a polynucleotide sequence of SEQ ID NO: 5, respectively.

In a second embodiment of the fourth aspect of the present disclosure, the polynucleotide encoding the di-alpha chain and the polynucleotide encoding the beta chain comprises a polynucleotide sequence of SEQ ID NO: 4 and a polynucleotide sequence of SEQ ID NO: 6, respectively.

In a third embodiment of the fourth aspect of the present disclosure, the host cell is selected from the group consisting of JM109 *E. coli* bacterial strain with lambda DE3, BL21-AI *E. coli* bacterial strain without lambda DE3, and SHuffle *E. coli* bacterial strain without lambda DE3.

In a fourth embodiment of the fourth aspect of the present disclosure, the host cell further comprises a polynucleotide encoding HemH.

In a fifth embodiment of the fourth aspect of the present disclosure, the host cell further comprises a polynucleotide encoding a Heme-transporter.

In a sixth embodiment of the fourth aspect of the present disclosure, the method further comprises the steps of:
(a) rupturing the host cell after the step of inducing the host cell to express recombinant hemoglobin to obtain a solution comprising the recombinant hemoglobin; and
(b) purifying the recombinant hemoglobin to obtain a purified recombinant hemoglobin.

In a firth aspect of the present disclosure, there is provided a system for producing the recombinant hemoglobin of the first aspect of the present disclosure, the system comprising: an *Escherichia coli* or non-*Escherichia coli* host cell comprising: a polynucleotide encoding HemH; a polynucleotide encoding a Heme-transporter; a polynucleotide encoding a di-alpha chain; and a polynucleotide encoding a beta chain, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the beta chain comprises a polypeptide sequence having at least 99.31% sequence homology with SEQ ID NO: 2, wherein the amino acid at position 1 must be methionine; or a polypeptide sequence having at least 97.94% sequence homology with SEQ ID NO: 3, wherein the amino acid at position 1 must be methionine, the amino acid at position 82 must be aspartic acid, and the amino acid at position 108 must be lysine.

Those skilled in the art will appreciate that the disclosure described herein is susceptible to variations and modifications other than those specifically described.

Other aspects and advantages of the disclosure will be apparent to those skilled in the art from a review of the ensuing description.

BRIEF DESCRIPTION OF THE DRAWINGS

FIG. 1 shows the polypeptide sequences for di-alpha chain SEQ ID NO: 1 and SEQ ID NO: 11 and beta chain SEQ ID NO: 2, SEQ ID NO: 3, and SEQ ID NO: 12 according to certain embodiments described herein.

FIG. 2A shows the plasmid maps, where pACYCDuet-CT is the vector carrying the ChuA gene and the gene for expressing TonB, and pET-HemHm1-TB is a general plasmid that carries the sequence for expressing HemH mutant and TB, where TB can be the sequence for expressing TBN, TBM1, or TBM9.

FIG. 5B shows a table of the p50 value of different recombinant human hemoglobins (TBN, TBM1, and TBM9) with and without 2,3-DPG according to certain embodiments described herein.

FIG. 7 shows the HemH mutant polynucleotide SEQ ID NO: 8 (top) and HemH mutant protein SEQ ID NO: 13 (bottom) according to certain embodiments described herein.

FIG. 8 shows the ChuA polynucleotide SEQ ID NO: 9 (top) and ChuA protein SEQ ID NO: 14 (bottom) according to certain embodiments described herein.

FIG. 9 shows the TonB polynucleotide SEQ ID NO: 10 (top) and TonB protein SEQ ID NO: 15 (bottom) according to certain embodiments described herein.

FIG. 14 shows body weight results after treating with recombinant human hemoglobin (TBM1) in Balb/c and ICR mice.

DETAILED DESCRIPTION OF THE INVENTION

Figure 2B:
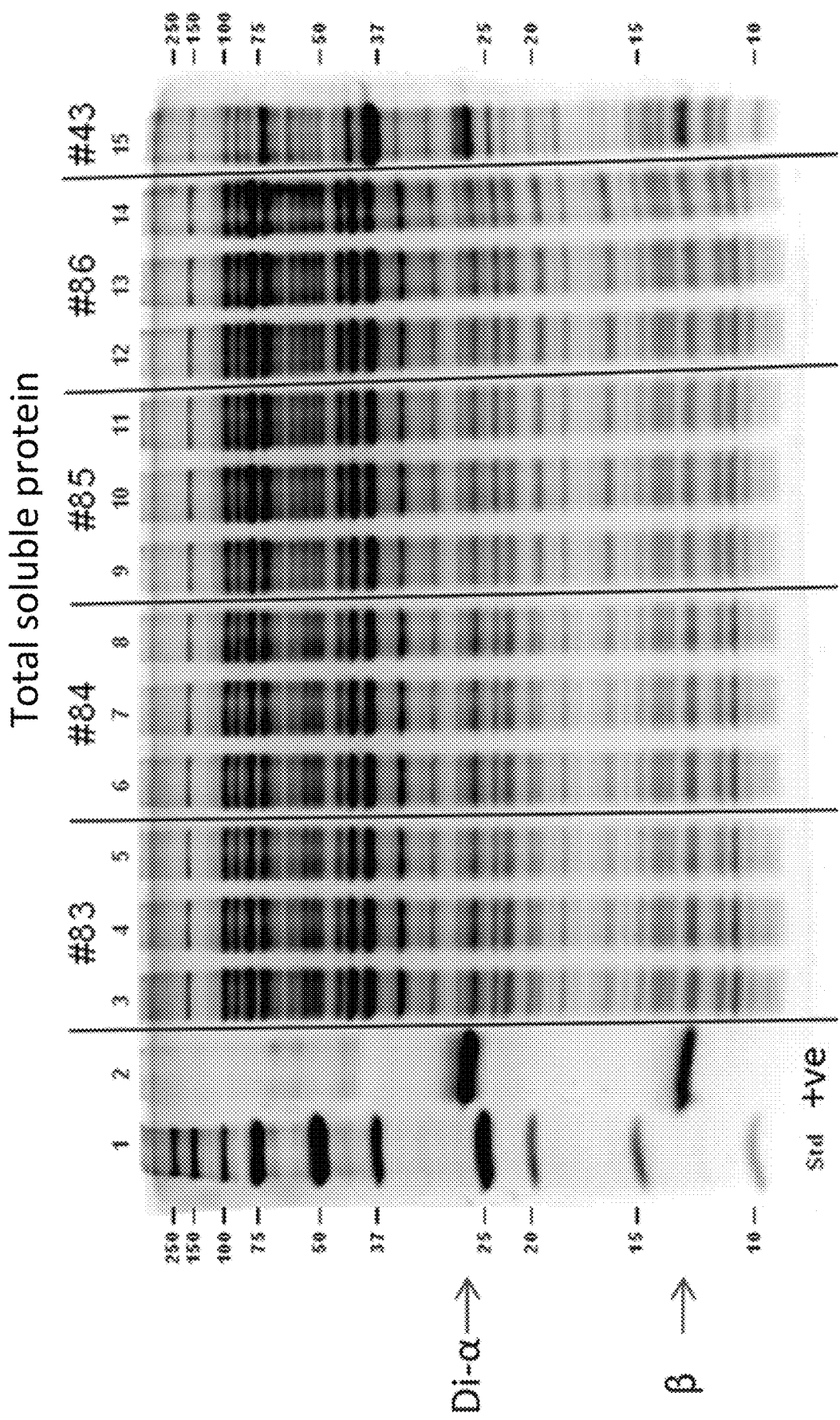
FIG. 2B shows the SDS-PAGE analysis of TBN, TBM1 and TBM9 expression in different cell strains by the plasmid in FIG. 2A, wherein #83 is the result for TBM1 expressed in SHuffle *E. coli* bacterial strain without lambda DE3, #84 is the result for TBM9 expressed in SHuffle *E. coli* bacterial strain without lambda DE3, #85 is the result for TBM1 expressed in JM109 T7CT CRISPR/Cas9 *E. coli* bacterial strain without lambda DE3, #86 is the result for TBM9 expressed in JM109 T7CT CRISPR/Cas9 *E. coli* bacterial strain without lambda DE3, and #43 is the result for TBN expressed in JM109 *E. coli* bacterial strain with lambda DE3.
Figure 2C:
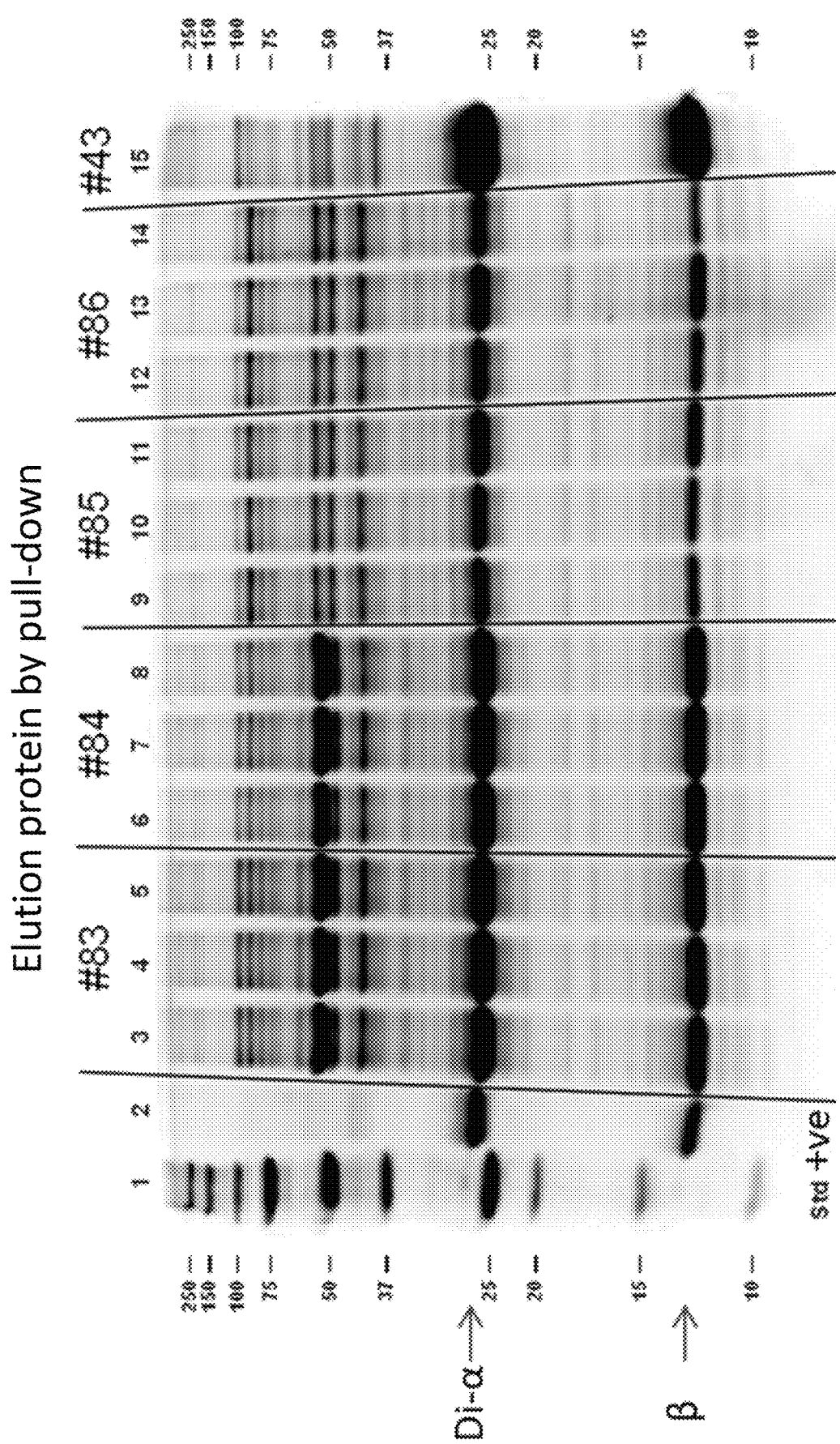
FIG. 2C shows the SDS-PAGE analysis of TBN, TBM1 and TBM9 expression in different cell strains by the plasmid in FIG. 2A, wherein #83 is the result for TBM1 expressed in SHuffle *E. coli* bacterial strain without lambda DE3, #84 is the result for TBM9 expressed in SHuffle *E. coli* bacterial strain without lambda DE3, #85 is the result for TBM1 expressed in JM109 T7CT CRISPR/Cas9 *E. coli* bacterial strain without lambda DE3, #86 is the result for TBM9 expressed in JM109 T7CT CRISPR/Cas9 *E. coli* bacterial strain without lambda DE3, and #43 is the result for TBN expressed in JM109 *E. coli* bacterial strain with lambda DE3.

The present disclosure relates to recombinant hemoglobins having high oxygen carrying capacity. The recombinant hemoglobins described herein comprise a di-alpha chain and two beta chains.

Definition of Terms

The definitions of terms used herein are meant to incorporate the present state-of-the-art definitions recognized for each term in the field of biotechnology. Where appropriate, exemplification is provided. The definitions apply to the terms as they are used throughout this specification, unless otherwise limited in specific instances, either individually or as part of a larger group.

The term "recombinant hemoglobin(s)" as used herein indicates a hemoglobin molecule and/or its variant with a molecular size of at least approximately 65 kDa and is synthesized by any standard molecular biology techniques rather than being isolated or purified from any animal or human source.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein, the term "amino acid", "amino acid monomer", or "amino acid residue" refers to any of the twenty naturally occurring amino acids including synthetic amino acids with unnatural side chains and including both D and L optical isomers. The terms "amino acid analog" and "analog" that are used interchangeably refer to an amino acid in which one or more individual atoms have been replaced, either with a different atom, isotope, or with a different functional group but is otherwise identical to its natural amino acid analog and have similar chemical and/or physical properties to its natural amino acid analog.

As used herein, the term "variant" refers to a polypeptide or polynucleotide sequence differing from a reference polypeptide or polynucleotide sequence, but retaining essential properties thereof. Generally, variants are overall closely similar, and, in many regions, identical to the reference polypeptide or polynucleotide sequence.

A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

The term "amino acid modification" as used herein indicates amino acid insertion, substitution, or deletion, etc. Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The term "nucleotide modifications" as used herein refers to nucleotide insertion, substitution, deletion, etc.

The term "percentage sequence homology", when used in reference to a polypeptide or polynucleotide sequence, refers to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions for the longer sequence in the window of comparison and multiplying the result by 100 to yield the percentage of sequence homology. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

As used herein, the terms "treat", "treating", "treatment", and the like refer to reducing or ameliorating a disorder and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith.

As used herein the term "stroke" indicates a medical condition in which poor blood flow to the brain results in cell death. It includes but not limited to ischemic stroke and hemorrhagic stroke.

As used herein, the term "hemorrhagic shock" refers to a condition of reduced tissue perfusion, resulting in the inadequate delivery of oxygen and nutrients that are necessary for cellular function.

The term "acute mountain sickness" as used herein refers to a condition developed when exposed to high altitudes having low levels of oxygen and decreased air pressure.

The term "ischemic disease" or "ischemia" as used herein refers to diseases and/or conditions characterized by reduced oxygenation to any tissue in the body such as, but not limited to, ischemic heart disease, transient ischemic attack, cardiac ischemia, stroke, reperfusion injury, bowel ischemia, intestinal ischemia, peripheral artery disease, critical limb ischemia, mesenteric ischemia, brain ischemia, leg ischemia, myocardial infarction, peripheral vascular disease, coronary artery disease, angina, wound healing, renal artery disease, diabetic ulcer healing, congestive heart failure, and hepatic ischemia. Ischemia can be caused by a number of conditions including, but not limited to, anemia, stroke and atherosclerosis. Multiple diseases result from ischemia including, for example, cerebrovascular ischemia, renal ischemia, pulmonary ischemia, limb ischemia, myocardial ischemia, and ischemic cardiomyopathy.

The term "peripheral artery disease" or "PAD" as used herein refers to a condition of narrowing of the peripheral arteries, such as those serving the legs, stomach, arms and/or head. PAD includes a wide range of vascular diseases caused by atherosclerotic, thromboembolic, and inflammatory processes that alter the structure and function of the arteries. The most common cause of PAD is atherosclerosis.

The term "p50 value" as used herein indicates the oxygen tension at which hemoglobin is 50% saturated. Values of p50 are negatively correlated with substrate affinity; lower values correspond to higher affinity and vice versa.

The term "oxygen carrying capacity" as used herein indicates the capability of a composition to carry oxygen. The capability to carry oxygen comprises but not limited to two aspects: compositions containing recombinant hemoglobins with lower oxygen affinity are used when rapid oxygenation is desired in cases of tissue hypoxia resulting from extensive blood loss (e.g., hemorrhagic shock). Lower oxygen affinity means that the material can "offload" oxygen to a target more easily than a material with a higher oxygen affinity. Compositions with higher oxygen affinity are useful as oxygenation adjunct therapies in cancer treatment where a slower delivery rate of oxygen is desired in that case. "Improved oxygen carrying capacity" means the level of oxygen carried by a composition is increased regardless of rapid oxygenation or low delivery of oxygen.

The terms "co-transform", "co-transforming", "co-transformed", and the like refer to a process that transfers more than one plasmids or vectors bearing exogenous DNA into the host cell at the same time. The host cells generally include but are not limited to bacterial, yeast, insect, mammalian, and plant cells. Any other reasonable host cells for accepting plasmids or vectors bearing exogenous DNA are also within the contemplation of the present disclosure. The methods for transformation of a DNA construct into a host cell include but not limited to chemical transformation, electroporation or particle bombardment. Any other reasonable methods for transforming a DNA construct into a host cell are also within the contemplation of the present disclosure. As used herein, the terms "plasmid", "expression plasmid", "vector", "DNA construct" and the like are used interchangeably herein to refer to a genetic structure that carries one or more exogenous DNA sequences of interest, as well as other functional DNA segments and/or sites, such as promoter segment, restriction site, 5' primer site, 3' primer site, origin of replication segment, antibiotic resistance gene segment, selectable marker segment, etc. These genetic structures are typically, but not always, circular DNA molecules, which are physically separated from a chromosomal DNA and can replicate independently. The terms "exogenous DNA", "exogenous DNA sequences of interest" and the like as used herein refer to deoxyribonucleic acid that originates outside of the host cells, including but not limited to the genes encoding particular proteins of interest or subunits thereof. The term "recombinant hemoglobin expression plasmid" as used herein can refer to a plasmid that carries a polynucleotide sequence encoding one di-alpha chain, a plasmid that carries a polynucleotide sequence encoding one or two beta chains, or a plasmid that carries a polynucleotide sequence encoding a di-alpha chain and a beta chain.

The term "HemH" as used herein refers to any enzyme, such as ferrochelatase, that catalyzes the production of heme. The term "Heme-transporter" as used herein refer proteins that facilitate the uptake of heme and/or iron, and such proteins include, but are not limited to, ChuA, TonB, heme carrier protein 1 (HCP1), divalent metal transporter 1 (DMT1), mucolipin-1 (also known as TRPML1), HRG1, and hemopexin.

The term "HemH plasmid" as used herein refers to a plasmid that carries a polynucleotide sequence encoding any enzyme, such as ferrochelatase, that catalyzes the production of heme, and the polynucleotide may include one or more nucleotide modifications. The term "Heme-transporter plasmid (s)" as used herein refer to one or more plasmids that carry one or more polynucleotide sequences encoding one or more proteins that facilitate the uptake of heme and/or iron, and such proteins include, but are not limited to, ChuA, TonB, heme carrier protein 1 (HCP1), divalent metal transporter 1 (DMT1), mucolipin-1 (also known as TRPML1), HRG1, and hemopexin.

The di-alpha chain can comprise a polypeptide sequence having at least 98.93% sequence homology with SEQ ID NO: 1. Polypeptides having at least 98.93% sequence homology to SEQ ID NO:1 can refer to polypeptides having at most three amino acid modifications, i.e. zero, one, two, or three amino acid modifications with respect to the SEQ ID NO: 1. In certain embodiments, the di-alpha chain comprises a polypeptide sequence having at least 99.29% sequence homology with the SEQ ID NO: 1. Polypeptides having at least 99.29% sequence homology can have at most two amino acid modifications, i.e. zero, one, or two amino acid modifications with respect to the SEQ ID NO: 1. In certain embodiments, the di-alpha chain comprises a polypeptide sequence having at least 99.64% sequence homology with the SEQ ID NO: 1. Polypeptides having at least 99.64% sequence homology can have at most one amino acid modifications, i.e. zero or one amino acid modification with respect to the SEQ ID NO: 1. In certain embodiments, the di-alpha chain comprises a polypeptide sequence of SEQ ID NO: 1. In certain embodiments, the di-alpha chain consists of a polypeptide sequence of SEQ ID NO: 1. The one, two, or three amino acid modifications can occur at any amino acid present in SEQ ID NO: 1, except the positions 1, 29, 58, 143, 171, and 200 of SEQ ID NO: 1, in which position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine.

The polypeptide sequence of the di-alpha chain can contain a linker that connects the N-terminal of a first alpha subunit with the C-terminal of a second alpha subunit or the N-terminal of a first alpha subunit is directly connected to the C-terminal of a second alpha subunit. In instances where a linker is presented in the di-alpha chain, the linker can be one or more amino acid residues selected from the group consisting of glycine and serine. In certain embodiments, the linker is $(Gly-Ser)_n$, $(Gly-Gly-Gly-Ser)_n$, $(Gly-Gly-Ser-Gly)_n$, $(Gly-Gly-Gly-Gly-Ser)_n$, $(Gly-Gly-Ser)n$, $(Gly-Ser)_n$ or $Gly_n$, wherein n is 1-10. In certain embodiments, the linker is $Gly_n$ linker, wherein n is 1-4. In certain embodiments, the linker is Gly.

Each of the two beta chains can comprise a polypeptide sequence having at least 97.94% sequence homology with SEQ ID NO: 2. Polypeptides having at least 97.94% sequence homology can have at most three amino acid modifications, i.e. zero, one, two, or three amino acid modifications with respect to the SEQ ID NO: 2. In certain embodiments, each of the two beta chains comprises a polypeptide sequence having at least 98.63% sequence homology with the SEQ ID NO: 2. Polypeptides having at least 98.63% sequence homology can have at most two amino acid modifications, i.e. zero, one, or two amino acid modifications with respect to the SEQ ID NO: 2. In certain embodiments, each of the two beta chains comprises a polypeptide sequence having at least 99.31% sequence homology with the SEQ ID NO: 2. Polypeptides having at least 99.31% sequence homology can have at most one amino acid modifications, i.e. zero or one amino acid modification with respect to the SEQ ID NO: 2. In certain embodiments, each of the two beta chains comprises a polypeptide sequence of SEQ ID NO: 2. In certain embodiments, the one, two, or three amino acid modifications can occur at any amino acid present in SEQ ID NO: 2, except the position 1 of the SEQ ID NO: 2, which must be methionine.

In certain embodiments, each of the two beta chains can comprise a polypeptide sequence having at least 97.94% sequence homology with SEQ ID NO: 3. Polypeptides having at least 97.94% sequence homology can refer to polypeptides having at most three amino acid modifications, i.e. zero, one, two, or three amino acid modifications with respect to the SEQ ID NO: 3. In certain embodiments, each of the two beta chains comprises a polypeptide sequence having at least 98.63% sequence homology with the SEQ ID NO: 3. Polypeptides having at least 98.63% sequence homology can have at most two amino acid modifications, i.e. zero, one, or two amino acid modifications with respect to the SEQ ID NO: 3. In certain embodiments, each of the two beta chains comprises a polypeptide sequence having at least 99.31% sequence homology with the SEQ ID NO: 3. Polypeptides having at least 99.31% sequence homology can have at most one amino acid modifications, i.e. zero or one amino acid modification with respect to the SEQ ID NO: 3. In certain embodiments, each of the two beta chains comprises a polypeptide sequence of SEQ ID NO: 3. The one, two, or three amino acid modifications can occur at any amino acid present in SEQ ID NO: 3, except the positions 1, 82, and 108 of the SEQ ID NO: 3, in which position 1 of the SEQ ID NO: 3 must be methionine, the position 82 of the SEQ ID NO: 3 must be aspartic acid, and the position 108 of the SEQ ID NO: 3 must be lysine.

Di-alpha chain having a polypeptide sequence of SEQ ID NO: 11 and two of the beta chains having a polypeptide sequence of SEQ ID NO: 12 form the recombinant hemoglobin TBN. Di-alpha chain having a polypeptide sequence of SEQ ID NO: 1 and two of the beta chains having a polypeptide sequence of SEQ ID NO: 2 form the recombinant hemoglobin TBM1. Di-alpha chain having a polypeptide sequence of SEQ ID NO: 1 and two of the beta chains having a polypeptide sequence of SEQ ID NO: 3 form the recombinant hemoglobin TBM9.

PPIX concentrations of TBN, TBM1, and TBM9 prepared under identical conditions are listed in Table 1. The p50 level, tetramer purity, met-hemoglobin (Met-Hb) % and heme/protein ratio are shown in Table 2. The methods for preparing the recombinant hemoglobins described herein are simplified and cost effective. Without wishing to be bound by theory, it is believed that the mutations of the di-alpha chain and beta chain lead to structural changes of the recombinant hemoglobins, which affects the kinetics of the incorporation of heme and PPIX, and ultimately changes the percentage of PPIX in the purified recombinant hemoglobins.

TABLE 1

PPIX % in different purified recombinant hemoglobins

| Recombinant hemoglobin | *PPIX % |
|---|---|
| TBN | 1.05 |
| TBM1 | 0.11 |
| TBM9 | 0.08 |

(*The PPIX % value is the average from five batches)

TABLE 2

Properties of purified recombinant hemoglobins

| Measurement | TBN | TBM1 | TBM9 |
|---|---|---|---|
| p50 level (mmHg) (with 2,3-DPG) | Raw: 14.86 Adair: 14.55 | Raw: 23.87 Adair: 25.38 | Raw: 35.80 Adair: 40.82 |
| Purity (Tetramer) (%) | 97.5 | 100 | 100 |
| Met-Hb (%) (by nanodrop method) | 6.6 | 3.8 | 3.2 |
| Heme/Protein ratio | 3.59 | 3.72 | 3.94 |

The present disclosure also relates to methods for expressing, fermenting, and purifying the recombinant hemoglobins described herein. In certain embodiments, the method comprises co-expressing the plasmids encoding the recombinant hemoglobins described herein, a ferrochelatase (HemH) plasmid, and a Heme-transporter plasmid in the host cells. Different host cells listed in Table 3 were tested, and among the host cells, JM109 (DE3) (with lambda DE3) (i.e. JM109 E. coli bacterial strain with lambda DE3), BL21-T7 or AI E. coli bacterial strain (without lambda DE3) and SHuffle® T7 Competent E. coli (without lambda DE3) (i.e. SHuffle E. coli bacterial strain without lambda DE3) have the best yield and quality. These four host cells are easily scalable, can express the plasmids transformed therewithin quickly, are very cheap, require simple culture conditions, and have established regulatory track record. The HemH plasmid can be wildtype or contain certain mutations. The Heme-transporter plasmid can be constructed by inserting the E. coli heme-utilization gene (ChuA) into a vector. The ChuA gene encodes a 69 kDa outer membrane protein, which facilitates the uptake of heme in E. coli. The uptake of heme by ChuA is dependent on an inner membrane protein named TonB. Therefore, the methods described herein preferably comprise a step of co-transforming the recombinant hemoglobin plasmids, the HemH plasmid, the ChuA plasmid, and the TonB plasmid into the selected host cells, i.e. JM109 E. coli bacterial strain with lambda DE3, BL21-T7 or AI E. coli bacterial strain without lambda DE3 and SHuffle E. coli bacterial strain without lambda DE3. Alternatively, the method can also co-transform the ChuA plasmid alone together with the recombinant hemoglobin plasmids and the HemH plasmid into the selected host cells.

The gene encoding the ferrochelatase (HemH) and the Heme-transporter can also be inserted into genome of E. coli bacterial strain by CRISPR/Cas9 genome editing method to endogenously express ferrochelatase (HemH) and the Heme-transporter. By this method, BL21-T7 and Jm109-T7 E. coli bacterial strain were modified to BL21-T7-CT (CRISPR/Cas9) and Jm109-T7-CT(CRISPR/Cas9) bacterial strains to express recombinant hemoglobin proteins.

TABLE 3

Different host cells

| No. | Strain | lambda DE3 |
|---|---|---|
| 1 | JM109 (DE3) | Y |
| 2 | BL21 (DE3) | Y |
| 3 | BLR (DE3) | Y |
| 4 | HMS174 (DE3) | Y |
| 5 | NovaBlue (DE3) | Y |
| 6 | Tuner (DE3) | Y |
| 7 | Origami 2 ™ (DE3) | Y |
| 8 | Origami B (DE3) | Y |
| 9 | Rosetta ™ 2 (DE3) | Y |
| 10 | Rosetta-gami (DE3) | Y |
| 11 | Rosetta-gami B (DE3) | Y |
| 12 | Rosetta Blue (DE3) | Y |
| 13 | BL21 Star (DE3) | Y |
| 14 | BL21 Super Star (DE3) | Y |
| 15 | T7 Express Competent E. coli (High Efficiency) | N |
| 16 | T7 Express lysY Competent E. coli (High Efficiency) | N |
| 17 | T7 Express lysY/Iq Competent E. coli (High Efficiency) | N |
| 18 | ScarabXpress T7lac | N |
| 19 | SHuffle ® T7 Competent E. coli | N |
| 20 | BL21-AI ™ One Shot ™ Chemically Competent E. coli | N |
| 21 | BL21-T7 | N |
| 22 | BL21-T7-CT (CRISPR/Cas9) | N |
| 23 | JM109-T7-CT (CRISPR/Cas9) | N |

(Y: Yes, N: No)

Figure 6:
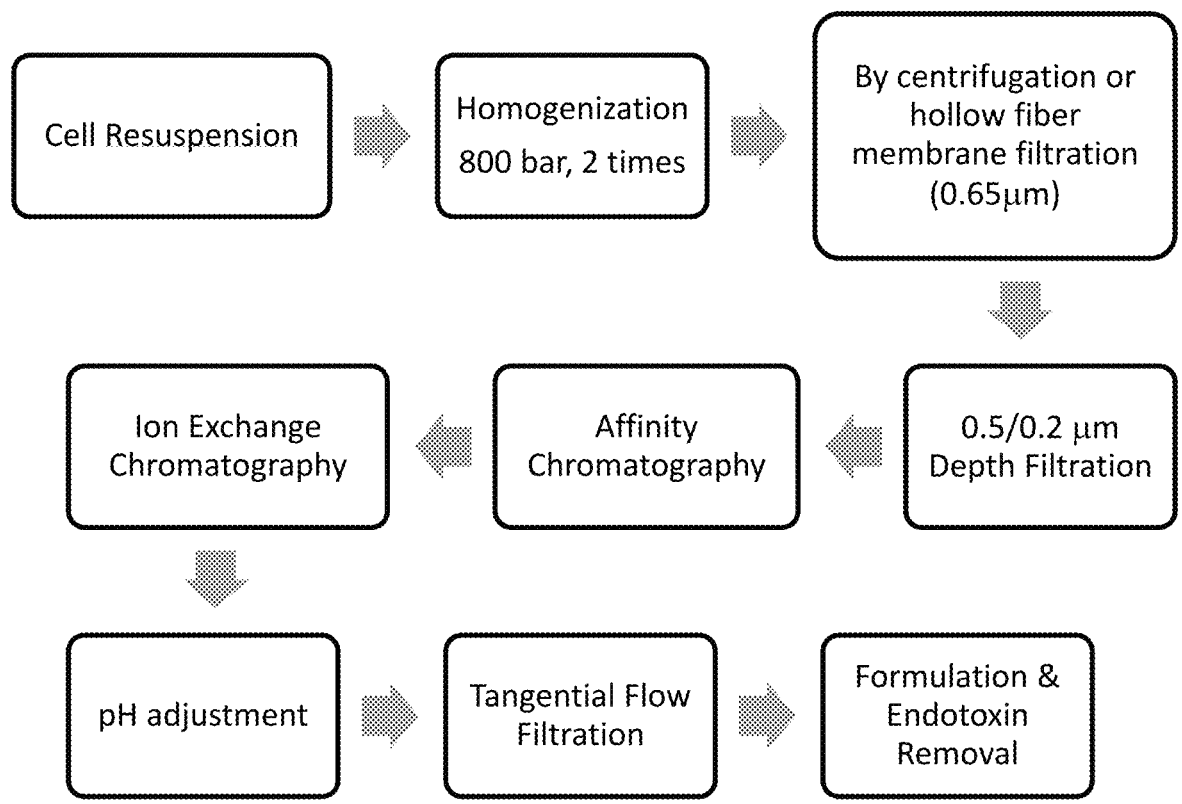
FIG. 6 shows a purification flow-chart according to certain embodiments described herein.

The method further comprises a purification step that advantageously does not require a heat step, and does not use carbon monoxide. The steps for purification are shown in FIG. 6. The recombinant hemoglobins prepared using the methods described herein can have reduced amounts of protoporphyrin-IX (PPIX), e.g., less than 1% (by weight), shown in Table 1. In certain embodiments, the recombinant hemoglobins prepared using the methods described herein have between 0.08% and 1%, 0.11% and 1%, 0.08% and 0.20%, 0.08% and 0.15%, or 0.08% and 0.11% (by weight) of PPIX. As such, the methods described herein are simpler as compared with existing methods for recombinant hemoglobin preparation, and can result in higher yield of soluble recombinant hemoglobin with reduced levels of impurities.

The present disclosure further relates to pharmaceutical compositions comprising the recombinant hemoglobins described herein and at least one pharmaceutically acceptable carrier. In certain embodiments, the pharmaceutical composition comprises other excipients, such as amino acids and sugar.

The present disclosure further relates to a polynucleotide sequence encoding a di-alpha chain as described herein. In certain embodiments, the polynucleotide sequence encodes a di-alpha chain comprising a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine. In certain embodiments, the polynucleotide sequence encodes a di-alpha chain comprising a polypeptide sequence having at least 99.29% sequence homology with the SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine. In certain embodiments, the polynucleotide sequence encodes a di-alpha chain comprising a polypeptide sequence having at least 99.64% sequence homology with the SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine. In certain embodiments, the polynucleotide sequence encodes a di-alpha chain comprising a polypeptide sequence of SEQ ID NO: 1. In certain embodiments, the polynucleotide sequence encodes a di-alpha chain consisting of a polypeptide sequence of SEQ ID NO: 1.

The present disclosure further relates to a polynucleotide sequence encoding a beta chain as described herein. In certain embodiments, the polynucleotide sequence encodes a beta chain comprising a polypeptide sequence having at least 97.94% sequence homology with SEQ ID NO: 2. In certain embodiments, the polynucleotide sequence encodes a beta chain comprising a polypeptide sequence having at least 98.63% sequence homology with the SEQ ID NO: 2. In certain embodiments, the polynucleotide sequence encodes a beta chain comprising a polypeptide sequence having at least 99.31% sequence homology with the SEQ ID NO: 2. In certain embodiments, the polynucleotide sequence encodes a beta chain comprising a polypeptide sequence comprising a polypeptide sequence of SEQ ID NO: 2. In certain embodiments, the polynucleotide sequence encodes a beta chain comprising a polypeptide sequence consisting of a polypeptide sequence of SEQ ID NO: 2.

In certain embodiments, the polynucleotide sequence encodes a beta chain comprising a polypeptide sequence having at least 97.94% sequence homology with SEQ ID NO: 3 In certain embodiments, the polynucleotide sequence encodes a beta chain comprising a polypeptide sequence having at least 98.63% sequence homology with the SEQ ID NO: 3. In certain embodiments, the polynucleotide sequence encodes a beta chain comprising a polypeptide sequence having at least 99.31% sequence homology with the SEQ ID NO: 3. In certain embodiments, the polynucleotide sequence encodes a beta chain comprising a polypeptide sequence comprising a polypeptide sequence of SEQ ID NO: 3. In certain embodiments, the acid modifications can occur at any amino acid present in SEQ ID NO: 3, except the positions 1, 82, and 108 of the SEQ ID NO: 3, in which position 1 of the SEQ ID NO: 3 must be methionine, the position 82 of the SEQ ID NO: 3 must be aspartic acid, and the position 108 of the SEQ ID NO: 3 must be lysine.

In certain embodiments, the polynucleotide sequence encodes a di-alpha chain as described herein and a beta chain as described herein. In certain embodiments, the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the two beta chains comprises a polypeptide sequence having at least 99.31% sequence homology with SEQ ID NO: 2, wherein the amino acid at position 1 must be methionine; or a polypeptide sequence having at least 97.94% sequence homology with SEQ ID NO: 3, wherein the amino acid at position 1 must be methionine, the amino acid at position 82 must be aspartic acid, and the amino acid at position 108 must be lysine.

The polynucleotides sequences described herein can be introduced into a desired cell using one or more vectors. A vector is a typically includes additional sequences, including sequences that direct propagation of the vector in the cell or insertion of part of the vector into the cell's genome, and a gene which allows an individual to screen for the presence of the vector. Common examples of vectors include plasmids, artificial chromosomes, viruses, and linear polynucleotide fragments which are designed to insert into a cell's genome. Vectors are well known tools to a person of ordinary skill in the art, and a person of ordinary skill in the art can easily find appropriate vectors for a particular organism in the literature or in biobanks, such as ATCC. In certain embodiments, provided herein is a vector comprising a polynucleotide sequence encoding at least one of a di-alpha chain described herein and a beta chain as described herein. In certain embodiments, the vector is a plasmid, artificial chromosomes, viruses, or a linear polynucleotide fragment, which is designed to insert into a cell's genome.

The present disclosure further relates to a system for producing a recombinant hemoglobin as described herein, the system comprising: an *Escherichia coli* or non-*Escherichia coli* host cell comprising: a polynucleotide encoding HemH; a polynucleotide encoding Heme-transporter; a polynucleotide encoding a di-alpha chain; and a polynucleotide encoding a beta chain; wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the beta chain comprises a polypeptide sequence having at least 99.31% sequence homology with SEQ ID NO: 2, wherein the amino acid at position 1 must be methionine; or a polypeptide sequence having at least 97.94% sequence homology with SEQ ID NO: 3, wherein the amino acid at position 1 must be methionine, the amino acid at position 82 must be aspartic acid, and the amino acid at position 108 must be lysine. In certain embodiments, the polynucleotide encoding HemH; the polynucleotide encoding Heme-transporter; the polynucleotide encoding the di-alpha chain; and the polynucleotide encoding the beta chain are present in one or more vectors selected from the group consisting of a plasmid, artificial chromosomes, viruses, and linear polynucleotide fragments which are designed to insert into a cell's genome. In certain embodiments, the polynucleotide encoding HemH; the polynucleotide encoding Heme-transporter; the polynucleotide encoding the di-alpha chain; and the polynucleotide encoding the beta chain are inserted into the host cell's genome using CRISPR/CAS 9. In certain embodiments, the polynucleotide encoding HemH; the polynucleotide encoding Heme-transporter; the polynucleotide encoding the di-alpha chain; and the polynucleotide encoding the beta chain are present in the host cell in one or more plasmids.

In certain embodiments, the system for producing the recombinant hemoglobin as described herein comprises: an *Escherichia coli* or non-*Escherichia coli* host cell comprising: a first plasmid comprising a polynucleotide encoding HemH, a di-alpha chain, and two beta chains, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the two beta chains comprises a polypeptide sequence having at least 99.31% sequence homology with SEQ ID NO: 2, wherein the amino acid at position 1 must be methionine; or a polypeptide sequence having at least 97.94% sequence homology with SEQ ID NO: 3, wherein the amino acid at position 1 must be methionine, the amino acid at position 82 must be aspartic acid, and the amino acid at position 108 must be lysine; and a second plasmid comprising a polynucleotide encoding Heme-transporter.

The vectors described herein can further comprise one or more polynucleotides encoding a promoter, an operator, and a selectable marker.

Any promoter can be used in the vectors described herein. The selection of the appropriate promoter is well within the skill of a person of ordinary skill in the art. Exemplary promoters include, but are not limited to, lac, trp, tac, trc, ara, araB, T5, T7, and T7lac.

Operators can include the lac operator, the λ operator, the trp operator, the gal operator, the ara operator, and the Arg operator. If desired, the corresponding promoter may be functionally associated with its operator.

A selectable marker can be a polynucleotide sequence that allows selection for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Any selectable marker in the art can be used in connection with the expression systems and methods described herein. Exemplary selectable markers include, but are not limited to, polynucleotide sequences that encode products which provide resistance against otherwise toxic compounds, such as antibiotics; polynucleotide sequences that encode a product which is otherwise lacking in the recipient cell, such as tRNA genes, auxotrophic markers); polynucleotide sequences that encode a product which suppresses the activity of a gene product; polynucleotide sequences that encode products which can be readily identified (e.g., phenotypic markers, such as β-galactosidase, green fluorescent protein (GFP), and cell surface proteins); and the like.

In certain embodiments, the selectable marker is a polynucleotide sequence that confers resistance against an antibacterial agent, such as ampicillin, kanamycin, erythromycin, chloramphenicol, gentamycin, kasugamycin, rifampicin, spectinomycin, D-Cycloserine, nalidixic acid, streptomycin, tetracycline, and the like.

The present disclosure further relates to a method of producing the recombinant hemoglobin as described herein, comprising the steps of: (a) providing a host cell comprising a polynucleotide encoding the di-alpha chain and a polynucleotide encoding the two beta chains; and (b) inducing the host cell containing the polynucleotide encoding the di-alpha chain and the polynucleotide encoding the two beta chains to express recombinant hemoglobin thereby producing the recombinant hemoglobin. In certain embodiments, the polynucleotide encoding HemH; the polynucleotide encoding Heme-transporter; the polynucleotide encoding the di-alpha chain; and the polynucleotide encoding the two beta chains are present in one or more vectors selected from the group consisting of a plasmid, artificial chromosomes, viruses, and linear polynucleotide fragments which are designed to insert into a cell's genome. In certain embodiments, the polynucleotide encoding HemH; the polynucleotide encoding Heme-transporter; the polynucleotide encoding the di-alpha chain; and the polynucleotide encoding the two beta chains are inserted into the host cell's genome using CRISPR/CAS 9. In certain embodiments, the polynucleotide encoding HemH; the polynucleotide encoding Heme-transporter; the polynucleotide encoding the di-alpha chain; and the polynucleotide encoding the two beta chains are present in the host cell in one or more plasmids.

In certain embodiments, the method of producing the recombinant hemoglobin described herein comprises: (a) providing a host cell comprising one or more recombinant hemoglobin expression plasmids encoding the di-alpha chain and the two beta chains; and (b) inducing the host cell containing the one or more recombinant hemoglobin expression plasmids encoding the di-alpha chain and the two beta chains to express recombinant hemoglobin thereby producing the recombinant hemoglobin.

In certain embodiments, the one or more recombinant hemoglobin expression plasmids encoding the di-alpha chain and the two beta chains comprise a polynucleotide sequence of SEQ ID NO: 4 and a polynucleotide sequence of SEQ ID NO: 5.

In certain embodiments, the one or more recombinant hemoglobin expression plasmids encoding the di-alpha chain and the two beta chains comprises a polynucleotide sequence of SEQ ID NO: 4 and a polynucleotide sequence of SEQ ID NO: 6.

In certain embodiments, the host cell is selected from the group consisting of JM109 E. coli bacterial strain with lambda DE3, BL21-AI E. coli bacterial strain without lambda DE3, and SHuffle E. coli bacterial strain without lambda DE3.

In certain embodiments, the host cell further comprises a plasmid encoding HemH.

In certain embodiments, the host cell further comprises one or two plasmids encoding a Heme-transporter.

Also provided herein, is a host cell comprising at least one vector described herein encoding at least one polypeptide selected from a di-alpha chain as described herein and two beta chains as described herein. In certain embodiments, the at least one vector is a plasmid. In certain embodiments, the host cell comprises one or more plasmids.

Recombinant hemoglobins can be formed by expressing one di-alpha chain and two beta chains inside a host cell in the presence of heme. Different host cells are tested and shown in Table 3. In some embodiments, the host cell is JM109 E. coli bacterial strain with lambda DE3, BL21-T7 or AI E. coli bacterial strain without lambda DE3, or SHuffle E. coli bacterial strain without lambda DE3 as they have the best yield, or BL21-T7-CT(CRISPR/Cas9) and Jm109-T7-CT(CRISPR/Cas9) as they have the best quality and easy manipulation. The expression of the di-alpha chain and beta chains can be realized by co-transforming a plasmid carrying the polynucleotide sequence that encodes one di-alpha polypeptide chain, and a plasmid carrying the polynucleotide sequence that encodes two beta polypeptide chains together into the host cell, wherein the ratio of the plasmid for di-alpha polypeptide chain and the plasmid for two beta polypeptide chains is approximately 1:1. The expression of the di-alpha chain and beta chains can also be realized by co-transforming a plasmid carrying the polynucleotide sequence that encodes one di-alpha polypeptide chain, and a plasmid carrying the polynucleotide sequence that encodes one beta polypeptide chain together into the host cell, wherein the ratio of the plasmid for di-alpha polypeptide chain and the plasmid for one beta polypeptide chain is approximately 1:2. The expression of the di-alpha chain and beta chain can also be realized by transforming a plasmid carrying both the polynucleotide sequence that encodes one di-alpha polypeptide chain and the polynucleotide sequence that encodes two beta chains into the host cells.

In certain embodiments, the plasmid for expressing the recombinant hemoglobins described herein comprise a polynucleotide encoding a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and two beta chains, each of which comprises a polypeptide sequence having at least 97.94% sequence homology with SEQ ID NO: 2, wherein position 1 of SEQ ID NO: 2 must be methionine. In some embodiments, the plasmid for expressing the recombinant hemoglobin comprises a polynucleotide sequence of SEQ ID NO: 4 (di-alpha chain for TBM1 and TBM9) and a polynucleotide sequence of SEQ ID NO: 5 (beta chain for TBM1). The plasmid maps are shown in FIG. 2A. In certain embodiments, the host cell is K12 strain (SHuffle® T7 Competent *E. coli*). In certain embodiments, the plasmid for expressing the recombinant hemoglobin comprises a polynucleotide sequence of SEQ ID NO: 4 (di-alpha chain for TBM1 and TBM9) and a polynucleotide sequence of SEQ ID NO: 5 (beta chain for TBM1) and the host cell is K12 strain (NEB # C3026).

In certain embodiments, the plasmid for expressing the recombinant hemoglobins described herein comprise a polynucleotide encoding a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and two beta chains, each of which comprises a polypeptide sequence having at least 97.94% sequence homology with SEQ ID NO: 3, wherein position 1 of SEQ ID NO: 3 must be methionine, position 82 of SEQ ID NO: 3 must be aspartic acid, and position 108 of SEQ ID NO: 3 must be lysine. In certain embodiments, the plasmid for expressing the recombinant hemoglobin comprises a polynucleotide sequence of SEQ ID NO: 4 (di-alpha chain for TBM1 and TBM9) and a polynucleotide sequence of SEQ ID NO: 6 (beta chain for TBM9) (the plasmid maps are shown in FIG. 2A) and the host cell is K12 strain (SHuffle® T7 Competent *E. coli*).

In certain embodiments, the plasmids for expressing di-alpha chain, beta chains and/or a combination thereof are co-transformed with the plasmid for expressing ferrochelatase or any other enzyme that catalyzes the production of heme. In certain embodiments, the plasmid for expressing ferrochelatase or any other enzyme that catalyzes the production of heme is a HemH plasmid, wherein the HemH plasmid can contain any HemH nucleotide. An exemplary HemH mutant polynucleotide is listed in FIG. 7. In certain embodiments, the HemH plasmid has a polynucleotide sequence of SEQ ID NO: 7 (wildtype) or SEQ ID NO: 8 (mutant).

In certain embodiments, hemin is added into the solution containing host cells that have been transformed with the plasmids expressing di-alpha chain, beta chains and/or a combination thereof.

In certain embodiments, a plasmid for expressing a heme transporter is also co-tranformed together with the plasmid for expressing the recombinant hemoglobin and/or the plasmid for expressing heme production enzymes. The heme transporter can be any protein that can facilitate the uptake of heme, including but not limited to a 69 kDa outer membrane protein encoded by the ChuA gene, and an inner membrane protein named TonB, on which the uptake of heme by ChuA is dependent. Any other heme and/or iron transporters, such as the heme carrier protein 1 (HCP1), divalent metal transporter 1 (DMT1), mucolipin-1 (also known as TRPML1), HRG1, hemopexin, and the like are also within the contemplation of the present disclosure.

In certain embodiments, the Heme-transporter plasmid comprises a polynucleotide sequence having 98% sequence homology with SEQ ID NO: 9. The DNA sequence of ChuA is shown in FIG. 8. In certain embodiments, the Heme-transporter plasmid comprises a polynucleotide sequence having 99% sequence homology with SEQ ID NO: 9. In certain embodiments, the Heme-transporter plasmid comprises a polynucleotide sequence of SEQ ID NO: 9.

In certain embodiments, the Heme-transporter plasmid comprises a polynucleotide sequence having 98% sequence homology with SEQ ID NO: 10. The DNA sequence encoding TonB is shown in FIG. 9. In certain embodiments, the Heme-transporter plasmid comprises a polynucleotide sequence having 99% sequence homology with SEQ ID NO: 10. In certain embodiment, the Heme-transporter plasmid comprises a polynucleotide sequence of SEQ ID NO: 10.

In certain embodiments, only the Heme-transporter plasmid bearing the ChuA is co-transformed with the plasmids for expressing di-alpha chain, beta chains and/or a combination thereof. In certain embodiments, only the Heme-transporter plasmid bearing the ChuA is co-transformed with the plasmids for expressing di-alpha chain, beta chains and/or a combination thereof, and the plasmid for expressing heme production enzymes. In certain embodiments, both the plasmid bearing the ChuA gene and the plasmid for expressing TonB are co-transformed with the plasmids for expressing di-alpha chain, beta chains and/or a combination thereof. In certain embodiments, both the plasmid bearing the ChuA gene and the plasmid for expressing TonB are co-transformed with the plasmids for expressing di-alpha chain, beta chains and/or a combination thereof, and the plasmid for expressing heme production enzymes.

In some embodiments, different protein expression systems have been tested (shown in Table 4) and the protein expression system for clone no. 12 and 19 show the best yield and quality of recombinant hemoglobin. The pETDuet-1 vector has two T7 promoters. The first T7 promoter is T1 and the second T7 promoter is T2. The proteins can be expressed under the control of either T1 or T2 of the pETDuet-1 vector. Similarly, the pRSFDuet-1 vector has two T7 promoters, and the first T7 promoter is R1 and the second T7 promoter is R2. The proteins can be expressed under the control of either T1 or T2 of the pRSFDuet-1 vector.

TABLE 4

Different protein expression systems

| Clone No. | Vectors and antibiotic resistance | Replicons | Copy Number | Expressed proteins Di − α + β | Ferrochelatase | Heme transporter |
|---|---|---|---|---|---|---|
| 1 | pETDuet-1 (Ampicillin) | ColE1 | ~40 | ✓ (T1) | | |
| 2 | | | | ✓ (T2) | | |
| 3 | | | | ✓ (T2) (β + Di − α) | | |
| 4 | | | | ✓ (T2) | ✓ (T1) | |
| 5 | | | | ✓ (T1) | ✓ (T2) | |
| 6 | | | | ✓ (T2) | M ✓ (T1) | |
| 7 | | | | ✓ (T1) | M ✓ (T2) | |
| 8 | pRSFDuet-1 (Kanamycin) | RSF1030 | >100 | ✓ (T2) | | |
| 9 | pETDuet-1 (Ampicillin) | ColE1 | ~40 | ✓ (T1) | | ✓ (R1) |
| 10 | pRSFDuet-1 (Kanamycin) | RSF1030 | >100 | ✓ (T2) | | ✓ (R2) |
| 12 | | | | ✓ (T1) | M ✓ (T2) | ✓ (R2) |
| 12 | | | | ✓ (T2) | M ✓ (T1) | ✓ (R2) |
| 13 | pETDuet-1 (Ampicillin) pACYCDuet-1 (Chloramphenicol) | ColE1 P15A | ~40 10-12 | ✓ (T2) | M ✓ (T1) | ✓ (A2) |
| 14 | pETDuet-1 (Ampicillin) pCDFDuet-1(Streptomycin) | ColE1 CloDF13 | ~40 20-40 | ✓ (T2) | M ✓ (T1) | ✓ (C2) |
| 15 | pRSFDuet-1 (Kanamycin) | RSF1030 | >100 | ✓ (R2) | M ✓ (R1) | ✓ (A2) |
| 16 | pACYCDuet-1 (Chloramphenicol) | P15A | 10-12 | ✓ (R1) | M ✓ (R2) | ✓ (A2) |
| 17 | pRSFDuet-1 (M) (Kanamycin) pACYCDuet-1 (Chloramphenicol) | RSF1030 P15A | >100 10-12 | ✓ (R1) | M ✓ (R2) | ✓ (A2) |
| 18 | pRSFDuet-1 (Kanamycin) | RSF1030 | >100 | ✓ (R2) | M ✓ (R1) | ✓ |
| 19 | pETDuet-1-Kana (Kanamycin) pACYCDuet-1 (Chloramphenicol) | ColE1 P15A | ~40 10-12 | ✓ (T2) | M ✓ (T1) | ✓ (A2) |

The components for the expression system contain (1) T7 promoter/lac operator and (2) sequence for protein expression including start codon and stop codon. Each of Duet plasmid has two T7 promoter/lac operator (T1 and T2). We inserted the different genes under control of $1^{st}$ or $2^{nd}$ T7 promoter/lac operator to test the protein expression level. The antibiotic resistance and replicons of plasmid were shown in Table 4. Clone no. 12 and 19 show the best yield and quality of recombinant hemoglobin. For clone 12, it contained two plasmids: $1^{st}$ plasmid is pETDuet-1 (ampicillin) which expressed di-alpha and beta chain under T1 and HemH under T2; $2^{nd}$ plasmid is pRSFDuet-1 (kanamycin) which expressed ChuA and TonB under R2. For clone 19, it contained two plasmids: $1^{st}$ plasmid is pETDuet-1-Kana (kanamycin) which expressed di-alpha and beta chain under T1 and HemH under T2; $2^{nd}$ plasmid is pACYCDuet-1 (chloramphenicol) which expressed ChuA and TonB under A2.

The host cells containing one or more of the above-mentioned plasmids can be incubated and fermented using any method known to those of skill in the art. The recombinant hemoglobins produced by the bacterial cells can then be purified using a simplified procedure, which does not require a heat step, and does not require the use of carbon monoxide (FIG. 6). The recombinant hemoglobins can be purified using the purification procedure described herein and can yield purified hemoglobin containing little or no HbCO, and having low amounts of PPIX, e.g., less than 1%. The UPLC results indicate that the heme:protein ratio is higher for TBM1 and TBM9, and highest for TBM9 (Table 2). The High Performance Liquid Chromatography (HPLC) results indicate the octamer:tetramer:dimer distribution of TBN, TBM1 and TBM9, as shown in Table 5 below.

TABLE 5

HPLC results for different recombinant hemoglobins

| Protein | Octamer % | Tetramer % | Dimer % |
|---|---|---|---|
| TBN | 2.50 | 97.50 | 0.00 |
| TBM1 | 0 | 100 | 0.00 |
| TBM9 | 0 | 100 | 0.00 |

Figure 4A:
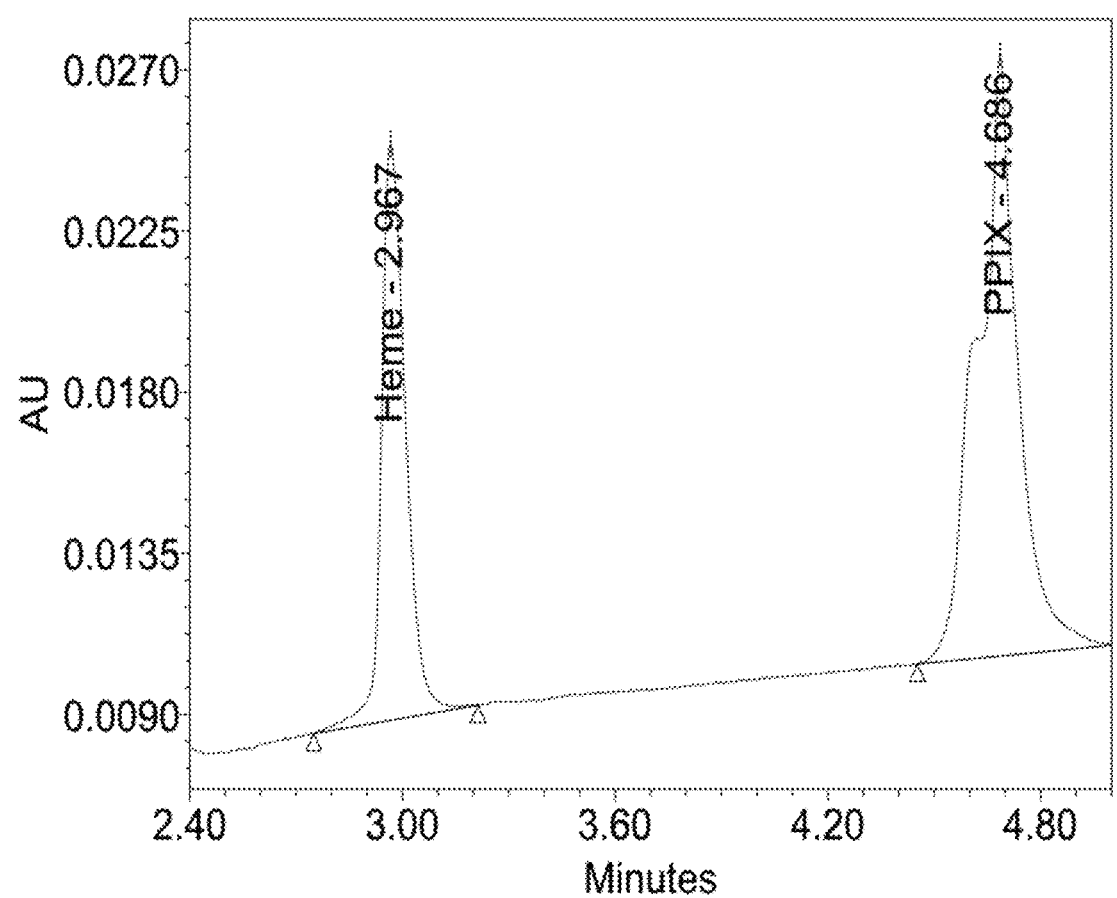
FIG. 4A shows a ultra-high performance liquid chromatography (UPLC) chromatogram showing the heme and PPIX levels of purified protein expressed using the previous plasmid comprising the nucleotide sequences of TBN (FIG. 4A).
Figure 4B:
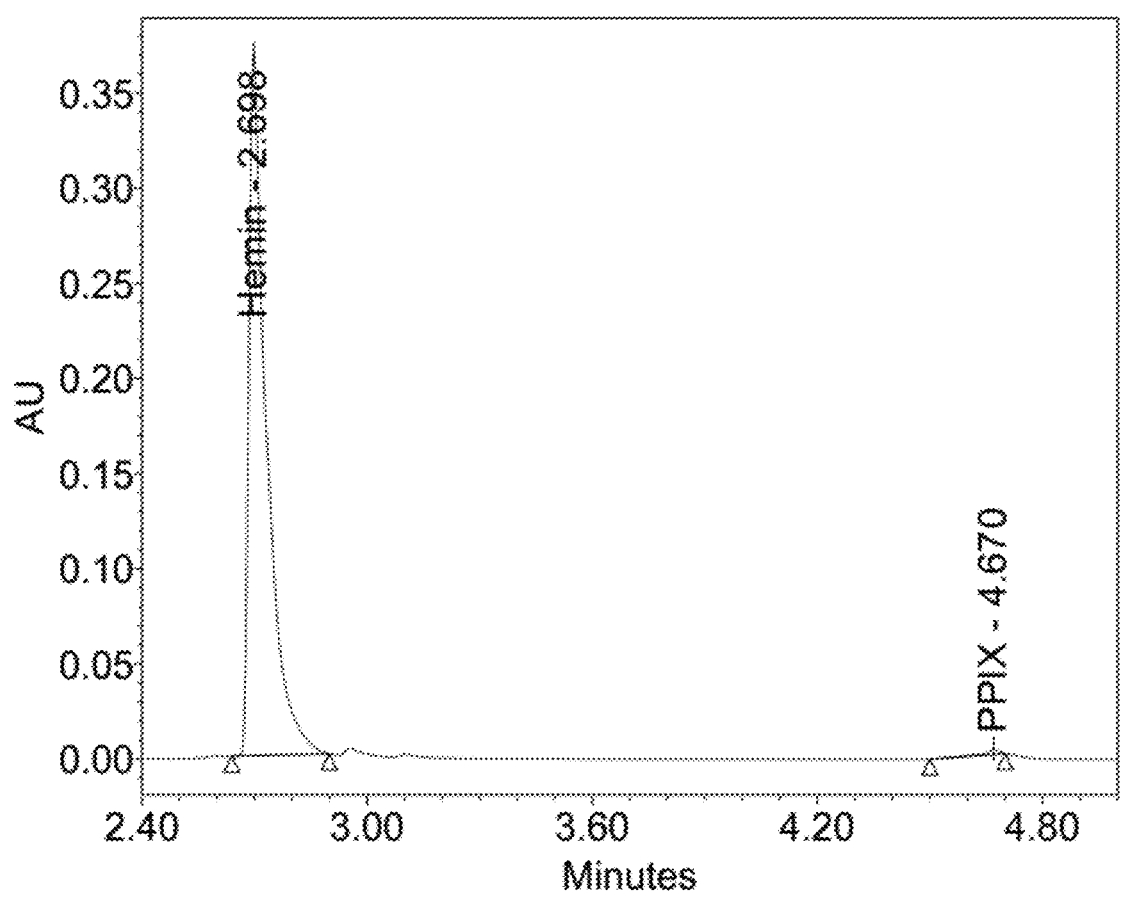
FIG. 4B shows a UPLC chromatogram showing the heme and PPIX level of purified protein expressed using the new improved plasmid comprising nucleotide sequences of HemH mutant, Heme transporter system (ChuA and TonB), and TBN (FIG. 4B).

Purification of the recombinant hemoglobins described herein can yield the protein product in high purity even without the step of heat treatment, as shown in FIG. 4 and Tables 1 and 2. Such unexpected technical effect solves one or more problems of the existing methods for preparing recombinant hemoglobins. For example, the stability of the recombinant hemoglobins described herein during the purification will not be affected and thus CO will not be required to maintain the stability of recombinant hemoglobins during heat treatment. Accordingly, an additional step to remove the undesired CO is not required. As such, the purification process for the recombinant hemoglobins described herein do not require heat treatment and CO removal, hence making the process simpler, less costly, and more industrially applicable.

Figure 3A:
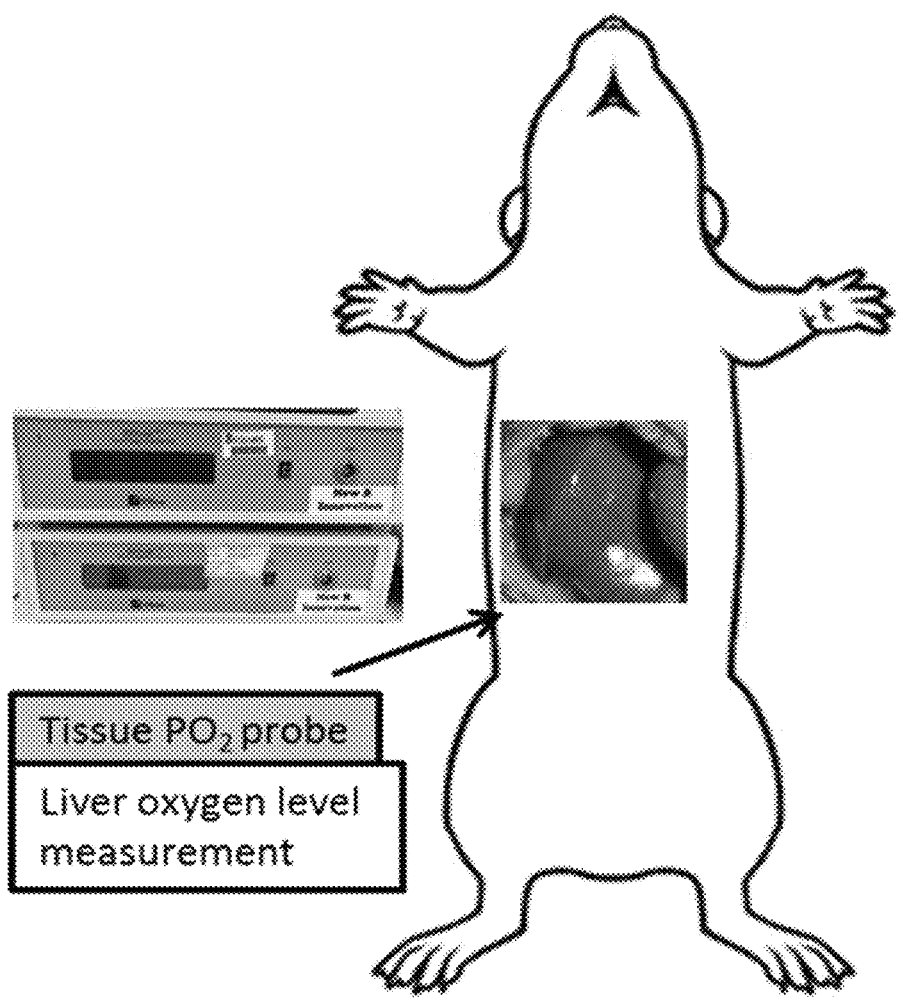
FIG. 3A shows the illustration of the liver oxygen level measurement in a mouse model.
Figure 3B:
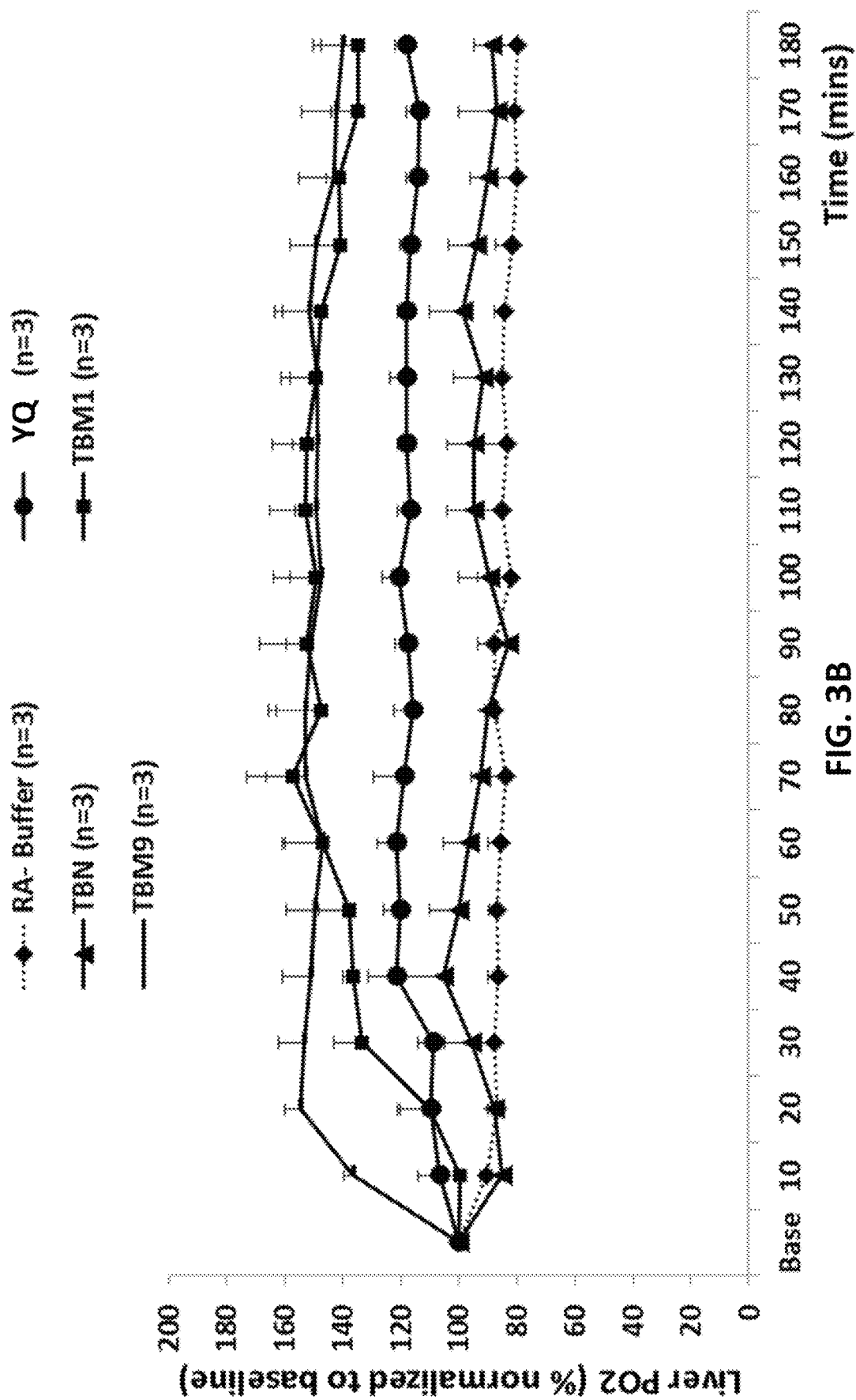
FIG. 3B shows the change of the liver oxygen level of the mouse model over 180 min after the administration of TBN, TBM1, TBM9, YQ (bovine fumaryl crosslinked Hb), and RA-buffer as a control.

The recombinant hemoglobins prepared using the methods described herein were injected in a mouse model to measure the liver oxygen level for 180 min (FIG. 3). Results showed that the recombinant hemoglobin TBM1, wherein the di-alpha chain has SEQ ID NO: 1 and the two beta chains have SEQ ID NO: 2, significantly increased the liver oxygen pressure at 30 min after being administered, as compared to the control group where buffer was administered and the YQ (bovine crossed-linked hemoglobin, batch no. ER007) was administered (FIG. 3B). The measurement of liver oxygen pressure over 180 min shows that the liver oxygen pressure reaches a plateau at 20-30 min after administering TBM9 and reaches a plateau at about 70 min after administering TBM1, both of which are higher than the plateaus reached by administering YQ, buffer, or TBN (wherein the di-alpha chain has SEQ ID NO: 11, and the two beta chains have SEQ ID NO: 12, as shown in FIG. 1). The p50 values of TBN, TBM1, and TBM9 are summarized in Table 6.

TABLE 6 p50 values and oxidation resistance of TBN, TBM1, and TBM9

Figure 10:
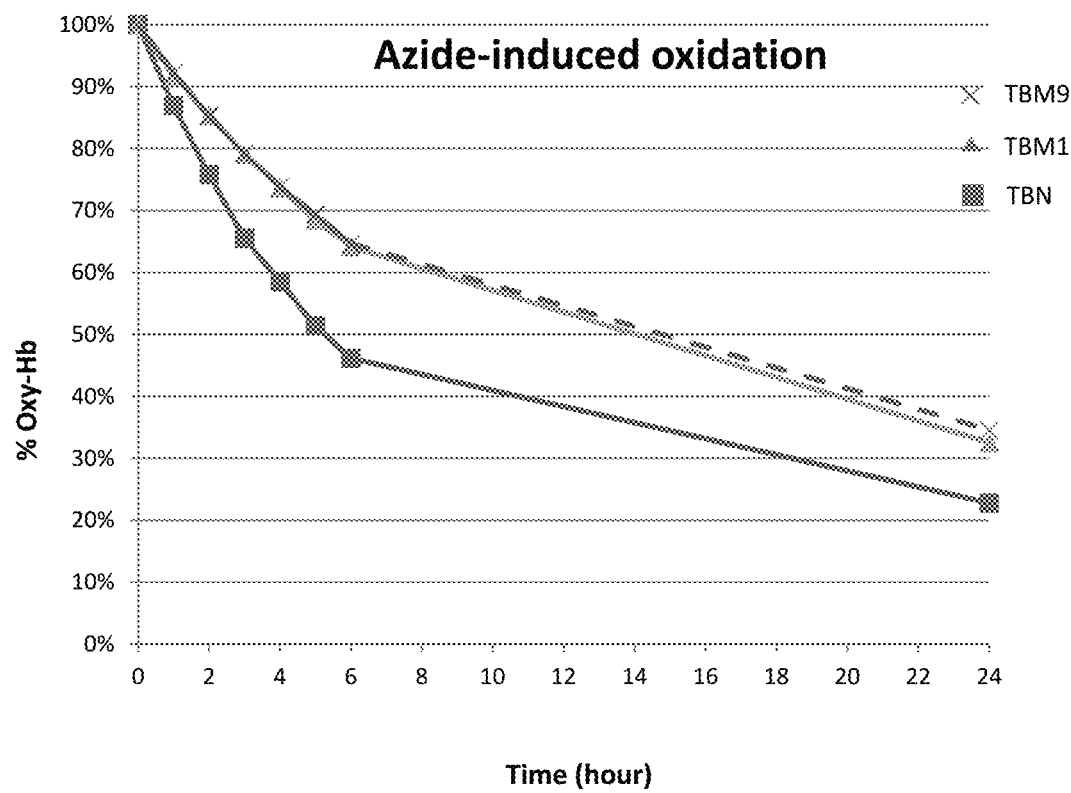
FIG. 10 shows a graph (top) and table (bottom) showing the azide-induced oxidation rates (kaz) values of TBN, TBM1, and TBM9.

| Recombinant hemoglobin | p50 (mmHg) | Resistance to oxidation (shown in FIG. 10) |
|---|---|---|
| TBN (di-α = SEQ ID NO: 11; 2 × β = SEQ ID NO: 12) | ~15 | Normal |
| TBM1 (di-α = SEQ ID NO: 1; 2 × β = SEQ ID NO: 2) | ~25 | Improved |
| TBM9 (di-α = SEQ ID NO: 1; 2 × β = SEQ ID NO: 3) | ~40 | Improved |

The recombinant hemoglobins described herein may be prepared as a pharmaceutical composition comprising at least one pharmaceutically acceptable carrier. Pharmaceutically acceptable carriers can comprise diluents, adjuvants, excipients, vehicles, or a combination thereof with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. In certain embodiments, such vehicle is sucrose or trehalose. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the protein in such pharmaceutical formulation can vary widely, e.g., from less than about 0.5%, usually at or at least about 1% to as much as 15 or 20% by weight and will be selected primarily based on required dose, fluid volumes, viscosities, etc., according to the particular mode of administration selected. Suitable vehicles and formulations comprise sucrose, trehalose, amino acid, phosphate buffer.

The recombinant hemoglobins described herein can be used as an agent for oxygenating in vivo or ex vivo tissues. Such agents are useful in the treatment of any disease or condition in which oxygen deficiency is the cause of the disease and/or condition, or oxygen deficiency is related to the treatment efficacy of the disease and/or condition. These diseases or conditions include, but not limited to, cancer, stroke, hemorrhagic shock, AMS, PAD, PD and, chronic obstructive pulmonary disease (COPD), emphysema, bronchitis, pneumonia, pulmonary edema, anemia, asthma, heart disease, diabetes, cystic fibrosis, epilepsy and seizures, inflammatory bowel disease (IBD), and Raynaud's disease. The required dosages of TBM1 and TBM9 can be significantly reduced as demonstrated by animal studies described herein.

The present disclosure also provides expression clones that can, e.g., improve the purity of recombinant hemoglobins described herein. As shown in FIG. 4 and Table 7, the purified protein expressed using the previous expression clone bearing nucleotide sequences of HemH and TBN, TBM1, or TBM9 has a peak for PPIX in the UPLC-PDA analysis, whereas such peak disappeared for the purified protein expressed using the new improved expression clone bearing nucleotide sequences of HemH mutant, Heme transporter system (ChuA and TonB), and TBN, TBM1, or TBM9. This shows that the expression clones described herein can significantly increase the percentage of heme incorporation in the produced hemoglobin, which improves the oxygen carrying function of the recombinant hemoglobins, and significantly decreases the PPIX, which is a byproduct and major impurity that can impair the oxygen carrying function of the produced recombinant hemoglobins.

TABLE 7

UPLC-PDA analysis results of heme and PPIX contents

|  | *PPIX % (wt/wt) | Standard Deviation |
|---|---|---|
| New clone (with HemH mutant and heme transporter system, ChuA + TonB): TBN | 1.05 | 0.38 |
| Old clone (With HemH wildtype, without heme transporter system, ChuA + TonB): TBN | 29.12 | 2.81 |

(*The PPIX % value is the average from three batches)

Figure 5A:
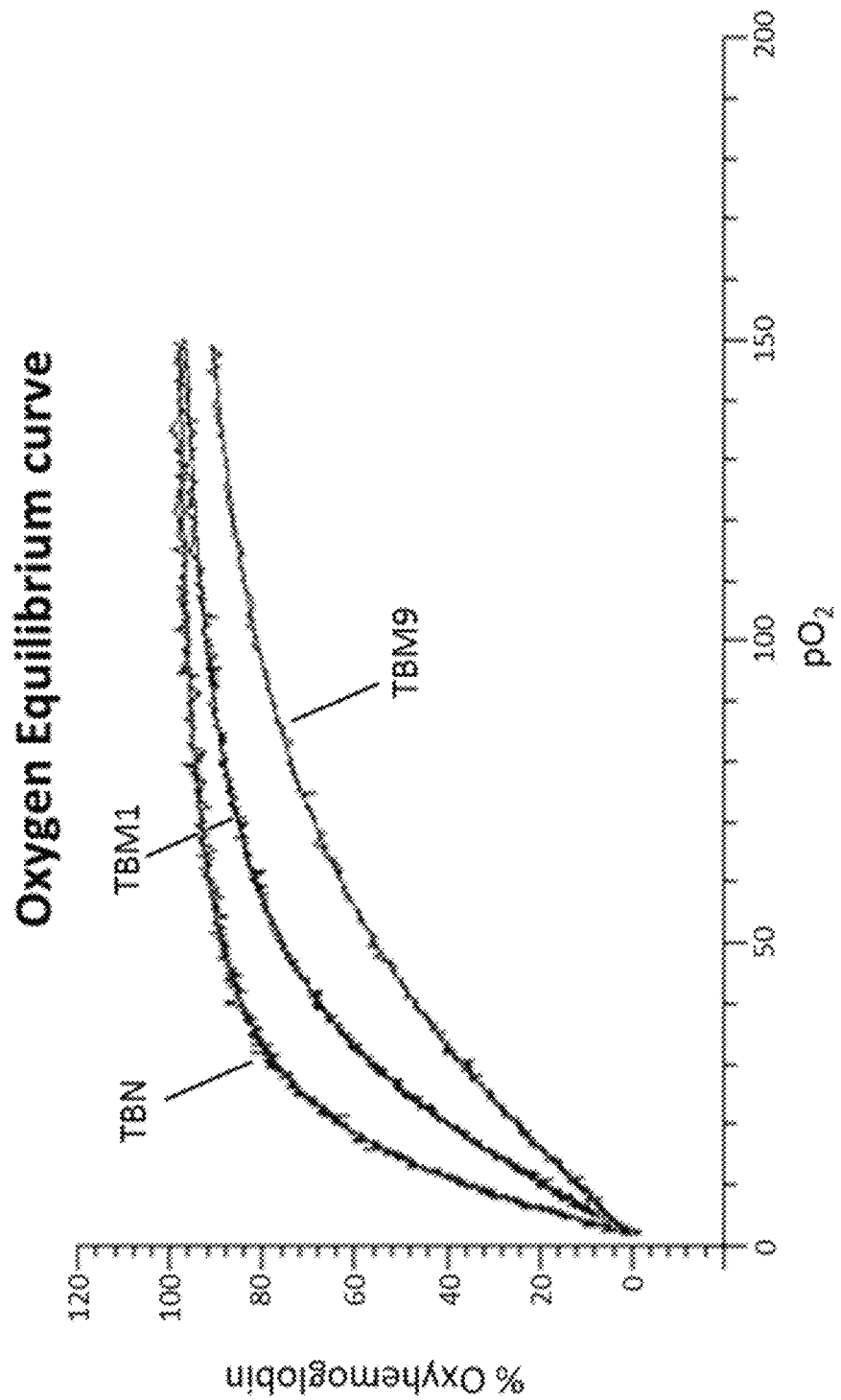
FIG. 5A shows the oxygen equilibrium curve for different recombinant human hemoglobins (TBN, TBM1, and TBM9) according to certain embodiments described herein.
Figure 5C:
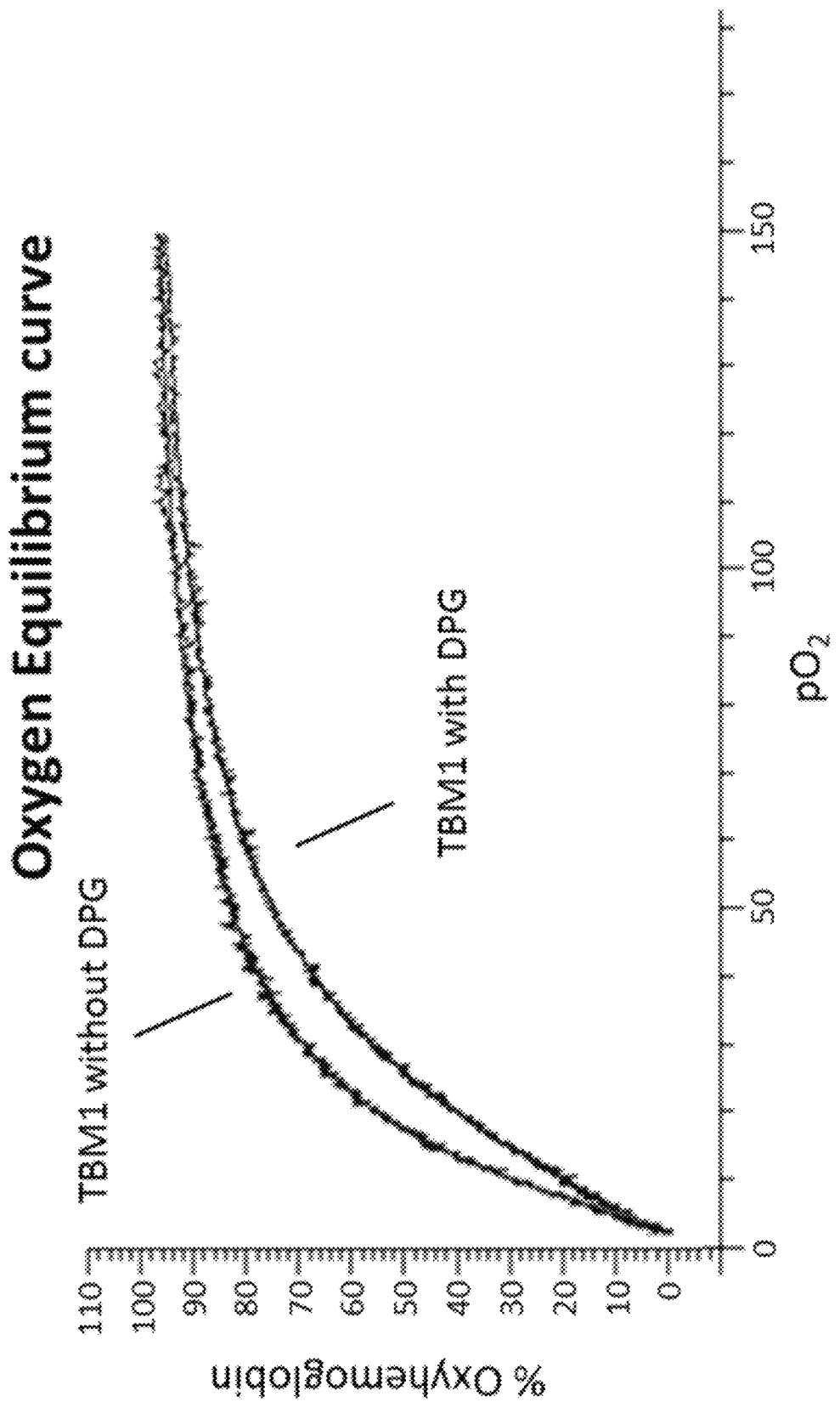
FIG. 5C shows an oxygen equilibrium curve of TBM1 with and without 2,3-DPG according to certain embodiments described herein.

To mimic in vivo conditions, the 2,3-DPG is added to the recombinant hemoglobin solution. The p50 value of human recombinant hemoglobin in the presence of 2,3-DPG increased as compared to the human recombinant without 2,3-DPG (FIG. 5B).

Example 1: Construction of TBN, TBM1, TBM9, HemH, ChuA, and TonB Expression Plasmids The plasmids were constructed in a conventional cloning method and the vectors and restriction enzyme cute sites used for each of the plasmids are indicated in the Table 8 below.

TABLE 8

Different plasmids information

| Plasmid Name | Insert | Vector Name | Restriction Enzyme Cut Site |
|---|---|---|---|
| pACYCDuet-CT | ChuA + TonB | pACYCDuet-1 | NdeI and PacI |
| pET-Hm-TBN-Kana | HemH(mutant); TBN | pETDuet-1-kana | XbaI and BamHI for HemH mutant; NdeI and PacI for TBN |
| pET-Hm-TBM1-Kana | HemH(mutant); TBM1 | pETDuet-1-kana | XbaI and BamHI for HemH mutant; NdeI and PacI for TBM1 |
| pET-Hm-TBM9-Kana | HemH(mutant); TBM9 | pETDuet-1-kana | XbaI and BamHI for HemH mutant; NdeI and PacI for TBM9 |

Example 2: Protein Expression

Small Scale Protein Expression: For Screening

The desired plasmids were transformed into the desired strains. From a fresh culture plate, colonies were picked and placed in a 15 ml tube containing 2 ml LB medium and appropriate antibiotic (Kanamycin 50 µg/ml; Chloramphenicol 34 µg/ml) and grown at 32° C. overnight, 250 rpm. The resulting cultures were diluted 1:100 into 10 ml TB medium with appropriate antibiotics in 50 ml falcon. When $OD_{600}$ reached 0.6, target proteins were induced by 0.4 mM IPTG at 25° C. After 20 h induction, the bacteria were harvest by centrifugation at 4000×g for 15 min.

Fermentation:

E. coli clones transformed with desired plasmids were inoculated into 200 ml of seed culture medium (6% yeast extract and 1% NaCl) and cultivated at 32° C. with shaking at 250 rpm for overnight. The fermentation was performed in 10-L bioreactor (Sartorius C plus). The flask of seed culture was inoculated into 6.5 L of medium (1% yeast extract, 1.6% tryptone, 15 mM $K_2HPO_4$, 37 mM $KH_2PO_4$, 15 mM NaCl, 15 mM $(NH_4)_2SO_4$, 2 mM L-proline, 2% glycerol) in a 10-L bioreactor with a final $OD_{600}$ at 0.05 and cultivated at 32° C. and pH 7.0 with airflow of 6 L/min and initial stir rate at 400 rpm, in which dissolved oxygen was maintained above 20%.

The fed-batch process of recombinant protein production in 10-L bioreactor was divided into two phases. The $1^{st}$ phase was aerobic batch cultivation at 32° C. for 7 h. The $2^{nd}$ Phase was an induction process at 25° C. for 18 h using isopropyl-β-d-thiogalactoside (IPTG) at a final concentration of 0.4 mM with $OD_{600}$ of bacteria at 4.0 to induce the expression of recombinant protein. A fed-batch cultivation at 25° C. for 18 h in which 80 g/L glycerol and 100 mg/L Hemin was fed continuously to maintain the required specific growth rate of bacteria with airflow of 8 L/min and stir rate at 600-800 rpm, in which dissolved oxygen was maintained ~4%. The bacteria at final $OD_{600}$ of 30-40 were harvested by centrifugation and stored in −80° C. for future use.

Example 3: Protein Purification

Small Scale Protein Purification by Nickel-Beads: For Screening

Cell pellet from 10 ml TB medium was suspended in a phosphate buffer (pH 7.4) and disrupted by 0.1 mm glass beads. The soluble protein was harvested by centrifugation at 15000×g for 15 min at 4° C. The target protein bound to nickel charged beads and eluted by 0.4 M Imidazole.

Protein Purification

Cell Lysis and Clarification of Crude Protein Sample

The cell pellet from fermentation was resuspended in a solubilization buffer (20 mM Tris-HCl, 150 mM NaCl, pH 8.5) in 1 g cell to 7 ml buffer ratio. The suspension was processed through a high-pressure homogenizer at 800 bar (two cycles). The cell lysate was clarified by hollow fiber system.

Chromatographic Purification

To remove impurities, the soluble fraction was passed through a series of chromatographic columns to isolate the TBN, TBM1, or TBM9 proteins.

First, the supernatant was loaded onto zinc affinity column. After sufficient column wash with buffer (20 mM Tris, 30 mM NaCl, pH 8.5), the target proteins were eluted by elution buffer (20 mM Tris, 100 mM imidazole, pH 8.3).

Second, the recovered fraction was loaded onto DEAE anion-exchange column. The target proteins were eluted by elution buffer (20 mM NaPi, pH 6.0).

Finally, the purified TBN/TBM1/TBM9 samples were concentrated to 50 mg/ml. The protein samples were lyophilized with appropriate excipients in a glass vial.

Example 4: Characterization of the Expressed Proteins (a) UPLC

The protein concentrations of the samples were measured by Bradford protein assay. Samples were diluted to protein concentration of about 10 mg/ml. A 50 µl of purified protein was mixed with 400 µl acidic acetone. After vigorous stirring, the mixture was separated by centrifugation. Acetonitrile (ACN, 400 µl, sample to organic solvent equals 1:8) was added into the solution, followed by centrifugation at 14,000 rpm for 5 min. Samples were then applied to UPLC analysis (Acquity H-class UPLC system; Waters, Milford, Mass., USA).

PPIX was separated by Waters Acquity UPLC® BEH C18 1.7 µm, 2.1×50 mm Column at 0.40 ml/min at 25° C. for 15 min (Eluent: A: $H_2O$; B: ACN [0.1% TFA]) Gradient: 30% B to 50% B in 6 min, 50% B to 80% B in 12 min, 80% B to 30% B in 13 min, 30% B in 15 min. (Detection wavelength at 400 nm). Commercially obtained PPIX (Sigma-Aldrich, St. Louis, Mo., USA) was used as the standard. The peak of PPIX was identified and the peak area in the calibration standards and samples was recorded. The peak area of calibration standards was plotted against the PPIX concentration of working standards. Thus, the relative amount of PPIX was obtained using the calibration curve and associated equation.

(b) High-Performance Liquid Chromatography (HPLC)

Samples were diluted to protein concentration about 1 mg/ml. A 10 µl of purified protein was applied to high-performance liquid chromatography (HPLC) analysis (Waters Breeze2 HPLC system; Waters, Milford, Mass., USA).

Proteins were separated by Yarra 3 µm, SEC-2000, 7.8× 300 mm Column at 0.50 ml/min at 25° C. for 20 min (Mobile phase: 0.75 M Magnesium Chloride, 0.2 M Tris, 116 µM EDTA). (Detection wavelength at 410 nm).

Example 5: Measurement of Oxygen-Carrying Capacity of the Recombinant Hemoglobins (a) Oxyhemoglobin Dissociation Curve (ODC) and p50 Value Measurement p50 value was determined by HEMOX-analyzer. 1.5 mg of purified protein were diluted in 3.5 ml of buffer (HEPES 100 mM, KCl 100 mM, pH7.3) with or without 2,3-DPG (4 mM). The sample buffer is drawn into a cuvette and the temperature of the mixture is equilibrated and brought to 37° C.; the sample is then oxygenated to 100% with air. After adjustment of the $pO_2$ value, the sample is deoxygenated with nitrogen. During the deoxygenation process, the curve is recorded. The p50 value is extrapolated on the x-axis as the point at which $O_2$ saturation is 50%.

(b) Liver Oxygen Level Measurement (180 Min) in a Rat Model

Liver tissue oxygenation (Liver $pO_2$) was directly monitored by the OxyLab® in vivo monitoring system (Oxford Optronix, UK) during the ischemia and reperfusion procedures in Buffalo rats. Briefly, a largearea-surface (LAS) oxygen sensor (Oxford Optronix, UK) was placed between the right hepatic lobe and triangle lobe of the rat livers. The branch of hepatic artery and portal vein to right and triangle lobes were clamped. YQ (bovine fumaryl cross-linked hemoglobin—positive control group) (0.2 g/kg), TBM1/ TBM9 (0.2 g/kg), or ringer's acetate buffer (control group) were administered intravenously. Liver oxygen tension was continuously measured during hepatic ischemia reperfusion injury: (1) baseline; (2) after infusion of YQ, TBM1/TBM9, or ringer's acetate buffer.

Example 6: Azide-Induced Oxidation Measurement

Recombinant hemoglobins were diluted to 1 mg/ml with 0.1 M sodium phosphate plus 1 mM EDTA at pH 7.0 at room temperature. Sample solution was oxygenated with compressed air by Hemox Analyzer (TCS scientific) for 20 min at room temperature. Azide-induced oxidation was started by adding 55.6 µl of 2 M sodium azide to 1 ml of oxygenated sample solution. The sample solution was then transferred without delay into cuvettes, sealing with parafilm to prevent evaporation. Visible spectra from 400 nm to 800 nm were recorded by Multiskan GO with AuDROP plate (thermos scientific) under room temperature in fast mode at 0, 1, 2, 3, 4, 5, 6, 24 and 48 h. Readings at 578 nm, 630 nm, and 700 nm were used to calculate the concentration of oxy-Hb with the equation below:

$$[oxy\text{-}Hb]=16.2*(A578-A700)-68*(A630-A700).$$

The initial rate of oxidation was calculated by an exponential fitting of the first 6 h of data.

Example 7: 4T1 Breast Cancer Cell Proliferation Study (a) 4T1 In Vitro Study

Figure 11:
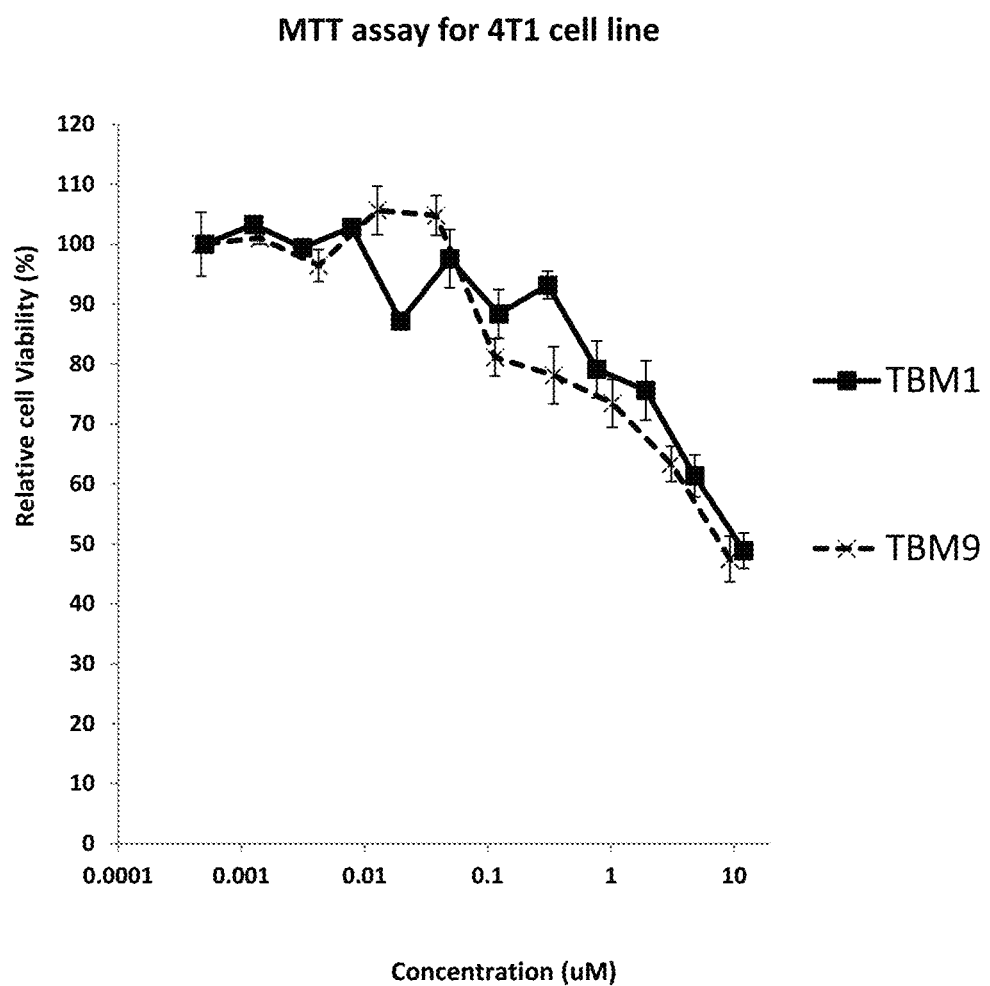
FIG. 11 shows MTT assay results for recombinant human hemoglobins TBM1 and TBM9 inhibiting 4T1 breast cancer cell proliferation in vitro.

To determine the inhibition of cancer cell proliferation in vitro, 4T1 breast cancer cells (2000 cells/well) were seeded onto 96-well plates and incubated for 24 h at 37° C. After cell stabilization, the culture medium was replaced with 100 ul of culture medium containing TBM1 or TBM9, cell viability was evaluated by MTT assay after 48 h. The results of the MTT assay on the cell proliferation after TBM1 or TBM9 treatment were shown in FIG. 11. TBM1 and TBM9 can significantly inhibit cancer cell proliferation at the concentration from 0.1 to 10 uM.

(b) 4T1 In Vivo Study—Mouse

Figure 12A:
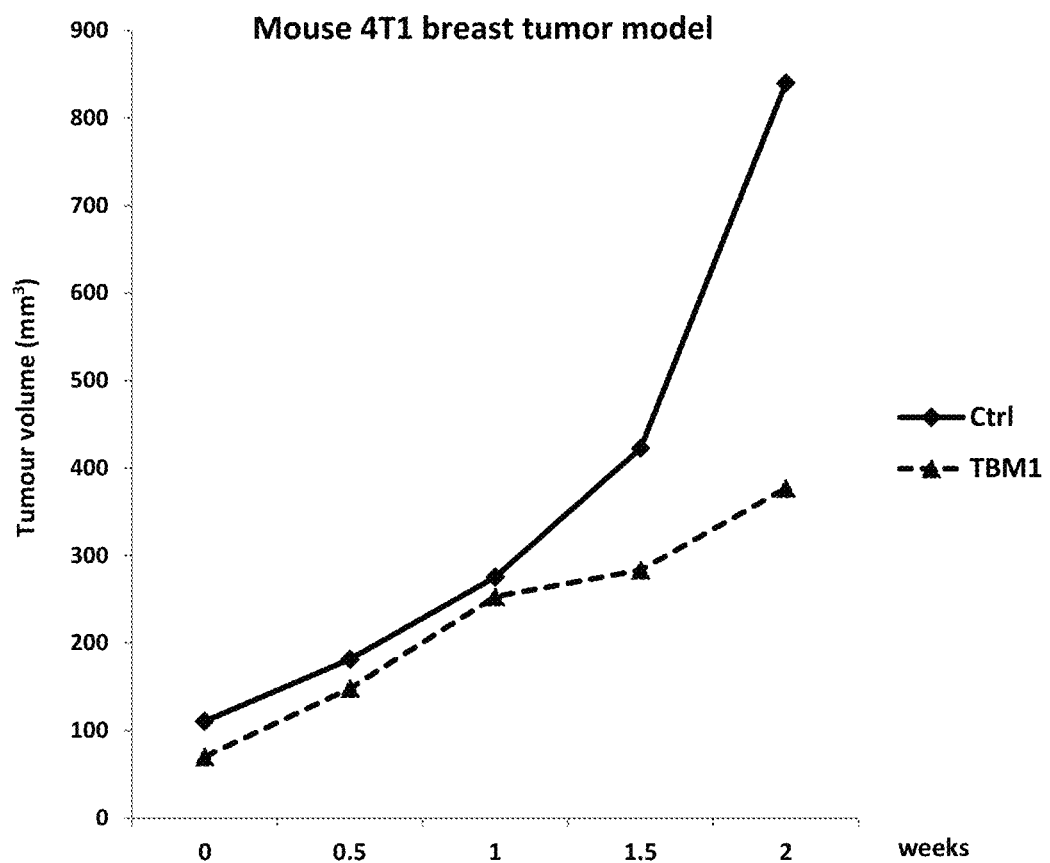
FIG. 12A show the recombinant human hemoglobins (TBM1) suppressing 4T1 breast cancer cell growth in vivo.
Figure 12B:
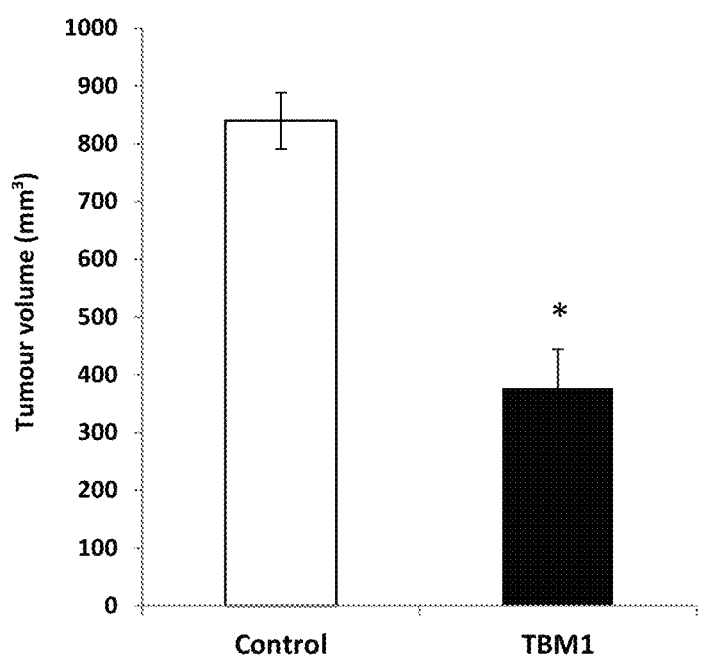
FIG. 12B shows a bar graph showing the recombinant human hemoglobins (TBM1) suppressing 4T1 breast cancer cell growth in vivo.

Six-week-old female BALB/c nude mice were subcutaneously injected with 4T1 cancer cells (5000 cells per mice). Tumor volume ($mm^3$) was calculated according to the following standard formula: (the longest diameter)×0.5×(the shortest diameter). After the tumor volume reached 100 $mm^3$, TBM1 protein (100 mg/kg, n=8) was injected by tail vein once per week for two weeks. The control group (n=8) was injected PBS. The tumor volume was monitored twice per week. As shown in FIG. 12A, tumors grew rapidly in mice treated with PBS (control group) in about 14 days after the treatment. Tumor growth was slowed down significantly in mice in TBM1 group compared with control groups (p<0.05). FIG. 12B showed tumor volume after 14 days treatments of TBM1. For control group, tumor reached a volume of 800 $mm^3$ which was substantially higher than that of the TBM1 treatment group (377 $mm^3$).

Example 8: Peripheral Arterial Disease (PAD) Model

A murine model was used to evaluate the potential therapeutic effect of TBM1 on critical limb ischemia. Briefly, mice were anesthetized by intraperitoneal injection of xylazine (20 mg/kg) and ketamine (100 mg/kg). The left femoral artery was excised and ligated from its proximal origin as a branch of the external iliac artery to the distal point where it bifurcates into the saphenous and popliteal arteries. 24 hours after successful femoral artery ligation, mice were randomly allocated to receive a single intravenous administration of normal saline (n=2) and TBM1 (800 mg/kg, n=2) via the tail veins.

Tissue perfusion of the hind limbs were assessed serially at baseline, immediate after femoral artery ligation, and on Day 7 after administration of the allocated treatments by using laser Doppler imaging system (Moor instruments, Devon, UK). Mice were anesthetized during the measurement procedure. The digital color-coded images were captured and analyzed to quantify blood flow in the region from the knee joint to the toes.

Figure 13:
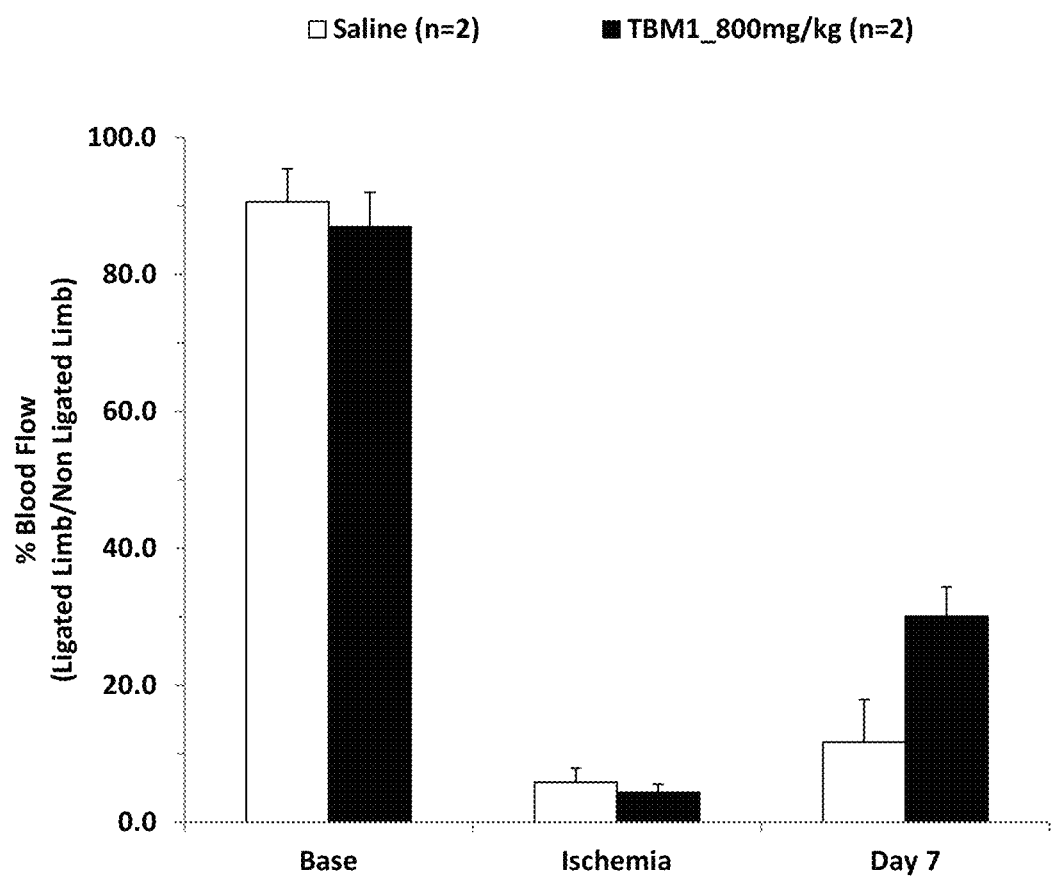
FIG. 13 shows the results of a murine PAD model results using saline and recombinant human hemoglobin (TBM1).

As shown in FIG. 13, In the time point of "immediate after right femoral artery ligation", our results showed the mean relative blood perfusion reduced substantially from 88.8% to only 5.2% of that the non-ischemic control limbs, confirming the successful induction of acute hind-limb ischemia. Interestingly, there was a large improvement in tissue blood perfusion in the ischemic limbs of mice receiving TBM1 treatment on Day 7. Specifically, the mean relative tissue blood perfusion was 11.7% of that of the non-ischemic control limbs in the normal saline group at Day 7, which was substantially lower than that of the counterparts receiving TBM1 at 800 mg/kg (30.1%).

In conclusion, single intravenous TBM1 injection at 800 mg/kg results in an improvement of tissue perfusion in a murine model of critical limb ischemia.

Example 9: Multiple Dose and Single Dose of TBM1 in Mice & Rat (a) Multiple Dose of TBM1 in Mice:

Mice (both Balb/C mice and ICR mice) were randomly divided into 3 groups (n=6) and received 4 consecutive weekly injections (TBM1 100, 200 mg/kg or PBS as a control) through the tail vein. At the endpoint, the mice were anesthetized and the blood samples were collected and analyzed for hematology analysis. The major organs (liver, spleen, kidney, lung) were harvested, fixed in formalin and processed for histological evaluation (H&E staining).

As shown in the FIG. 14, no significant differences in weights were seen between the TBM1 treatment groups and control group (both for Balb/C mice and ICR mice). Other usual signs of drug toxicity in mice, such as ruffled fur, anorexia, cachexia, skin tenting (due to dehydration), skin ulcerations, or toxic deaths were not seen at the doses used.

(b) Single Dose of TBM1 in Rat (for Checking Cardiomyopathy):

SD rats (n=6) were received single dose (TBM1 400 and 800 mg/kg, by intravenous infusion). Briefly, jugular catheter was surgically implanted into the right jugular vein of the rats at least 4 days before the dosing day. On the dosing day, animals were weighted and assigned into 6 per groups with half numbers of male and female. TBM1 was drawn into syringe and connected to an extension tube with a 0.22 um filter for injection. The infusion was given at a constant rate by motorized syringe pump. After 72 h, the rats were sacrificed and the hearts were harvested, fixed in formalin and processed for histological evaluation (H&E staining). There was no evidence of drug induced cardiomyopathy in total six rats.

Although the invention has been described in terms of certain embodiments, other embodiments apparent to those of ordinary skill in the art are also within the scope of this invention. Accordingly, the scope of the invention is intended to be defined only by the claims which follow.

INDUSTRIAL APPLICABILITY

The present disclosure provides recombinant hemoglobins useful for treating oxygen deficiency related diseases or conditions, such as cancer, stroke, hemorrhagic shock, acute mountain sickness (AMS), peripheral arterial disease (PAD) and Parkinson's disease (PD). The recombinant hemoglobins described herein can have increased oxygen carrying capacity. The therapeutic use of the pharmaceutical compositions comprising the recombinant hemoglobins described herein can require a reduced clinical dosage, which increases the safety of such therapeutic use in a subject in need thereof. Also provided are simplified methods and/or processes to prepare, obtain, ferment, and/or purify the recombinant hemoglobins with high yield and high purity. Such methods can be used at an industrial scale, which can be more cost effective and less impurity-prone as compared to existing conventional methods.

We claim:

1. A recombinant human hemoglobin comprising a di-alpha chain and two beta chains, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine and wherein said recombinant human hemoglobin has higher stability and/or increases oxygen transport as compared to unmodified human hemoglobin.

2. The recombinant hemoglobin of claim 1, wherein the di-alpha chain comprises a polypeptide sequence having at least 99.29% sequence homology with SEQ ID NO: 1.

3. The recombinant hemoglobin of claim 2, wherein the di-alpha chain comprises a polypeptide having at least 99.64% sequence homology with SEQ ID NO: 1.

4. The recombinant hemoglobin of claim 3, wherein the di-alpha chain is a polypeptide sequence having SEQ ID NO: 1.

5. The recombinant hemoglobin of claim 1, wherein each of the two beta chains comprises a polypeptide sequence having at least 97.94% sequence homology with SEQ ID NO: 2, wherein the amino acid at position 1 must be methionine.

6. The recombinant hemoglobin of claim 5, wherein each of the two beta chains is a polypeptide sequence having SEQ ID NO: 2.

7. The recombinant hemoglobin of claim 1, wherein each of the two beta chains comprises a polypeptide sequence having at least 97.94% sequence homology with SEQ ID NO: 3, wherein the amino acid at position 1 must be methionine, the amino acid at position 82 must be aspartic acid, and the amino acid at position 108 must be lysine.

8. The recombinant hemoglobin of claim 7, wherein each of the two beta chains comprises a polypeptide sequence having at least 98.63% sequence homology with SEQ ID NO: 3.

9. The recombinant hemoglobin of claim 8, wherein each of the two beta chains comprises a polypeptide sequence having at least 99.31% sequence homology with SEQ ID NO: 3.

10. The recombinant hemoglobin of claim 9, wherein each of the two beta chains comprises a polypeptide sequence of SEQ ID NO: 3.

11. A pharmaceutical composition comprising the recombinant hemoglobin of claim 1 and at least one pharmaceutically acceptable carrier.

12. A method of treating an oxygen deficiency related disease in a subject in need thereof comprising the step of administering a therapeutically effective amount of the pharmaceutical composition of claim 11 to the subject.

13. The method of claim 12, wherein the oxygen deficiency related disease comprises cancer, stroke, hemorrhagic shock, acute mountain sickness (AMS), peripheral arterial disease (PAD), or Parkinson's disease (PD).

14. A method of producing the recombinant hemoglobin of claim 1, comprising the steps of:
    (a) providing a host cell comprising a polynucleotide encoding the di-alpha chain and a polynucleotide encoding a beta chain of claim 1; and
    (b) inducing the host cell containing the polynucleotide encoding the di-alpha chain and the polynucleotide encoding the beta chain to express recombinant hemoglobin thereby producing the recombinant hemoglobin of claim 1.

15. The method of claim 14, wherein the polynucleotide encoding the di-alpha chain and the polynucleotide encoding the beta chain comprise a polynucleotide sequence of SEQ ID NO: 4 and a polynucleotide sequence of SEQ ID NO: 5, respectively.

16. The method of claim 14, wherein the polynucleotide encoding the di-alpha chain and the polynucleotide encoding the beta chain comprises a polynucleotide sequence of SEQ ID NO: 4 and a polynucleotide sequence of SEQ ID NO: 6, respectively.

17. The method of claim 14, wherein the host cell is selected from the group consisting of JM109 E. coli bacterial strain with lambda DE3 vector, BL21-AI E. coli bacterial strain without lambda DE3 vector, and SHuffle E. coli bacterial strain without lambda DE3 vector.

18. The method of claim 14, wherein the host cell further comprises a polynucleotide encoding bacterial ferrochelatase "HemH".

19. The method of claim 14, wherein the host cell further comprises a polynucleotide encoding a Heme-transporter.

20. The method of claim 14 further comprising the steps of:
- (a) rupturing the host cell after the step of inducing the host cell to express recombinant hemoglobin to obtain a solution comprising the recombinant hemoglobin; and
- (b) purifying the recombinant hemoglobin to obtain a purified recombinant hemoglobin.

21. A system for producing the human recombinant hemoglobin of claim 1, the system comprising:

an *Escherichia coli* or non-*Escherichia coli* host cell comprising:

a polynucleotide encoding a bacterial HemH; a polynucleotide encoding a bacterial Heme-transporter; a polynucleotide encoding the di-alpha chain, and a polynucleotide encoding the beta chain, wherein the di-alpha chain comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine; and the beta chain comprises a polypeptide sequence having at least 99.31% sequence homology with SEQ ID NO: 2, wherein the amino acid at position 1 must be methionine; or a polypeptide sequence having at least 97.94% sequence homology with SEQ ID NO: 3, wherein the amino acid at position 1 must be methionine, the amino acid at position 82 must be aspartic acid, and the amino acid at position 108 must be lysine.

\* \* \* \* \*